United States Patent
Yamamoto et al.

(10) Patent No.: US 7,171,250 B2
(45) Date of Patent: Jan. 30, 2007

(54) LIVING BODY LIGHT MEASUREMENT SYSTEM AND SIGNAL PROCESSING METHOD

(75) Inventors: Tsuyoshi Yamamoto, Matsudo (JP); Atsushi Maki, Fuchu (JP); Takusige Katura, Hatoyama (JP); Hideo Kawaguchi, Hatoyama (JP)

(73) Assignee: Hitachi, Ltd., Tokyo (JP)

( * ) Notice: Subject to any disclaimer, the term of this patent is extended or adjusted under 35 U.S.C. 154(b) by 265 days.

(21) Appl. No.: 11/010,668

(22) Filed: Dec. 14, 2004

(65) Prior Publication Data

US 2005/0192490 A1 Sep. 1, 2005

(30) Foreign Application Priority Data

Feb. 26, 2004 (JP) .............................. 2004-050741

(51) Int. Cl.
*A61B 5/00* (2006.01)
(52) U.S. Cl. ...................... 600/310; 600/322; 600/323; 600/340; 600/344
(58) Field of Classification Search ................ 600/310, 600/322, 323, 340, 344
See application file for complete search history.

(56) References Cited

U.S. PATENT DOCUMENTS 5,803,909 A * 9/1998 Maki et al. .................. 600/310
5,853,370 A * 12/1998 Chance et al. ............... 600/323
6,542,763 B1 * 4/2003 Yamashita et al. .......... 600/310

OTHER PUBLICATIONS

Kadoya, Takuma, et al, "Phantom experiment on relationship between activated position of cerebral cortex and NIR signal", 2001, Proceedings of SPIE vol. 4250, pp. 558-565.

Atsushi Maki et al., "Spatial and Temporal Analysis of Human Motor Activity Using Noninvasive NIR Topography", Medical Physics, Dec. 1995, vol. 22, No. 12, pp. 1997-2005.
Eiju Watanabe et al., "Noninvasive Cerebral Blood Volume Measurement During Seizures Using Multichannel Near Infrared Spectroscopic Topography", Journal of Biomedical Optics, Jul. 2000, vol. 5, No. 3, pp. 287-290.
Eiju Watanabe et al., "Non-invasive Assessment of Language Dominance with Near-Infrared Spectroscopic Mapping", Neuroscience Letters, vol. 256 (1998), pp. 49-52.
Tsuyoshi Yamamoto et al., "Arranging Optical Fibres for the Spatial Resolution Improvement of Topographical Images", Physics in Medicine and Biology, vol. 47 (2002), pp. 3429-3440.
David T. Sandwell, "Biharmonic Spline Interpolation of GEOS-3 and SEASAT Altimeter Data", Geophysical Research Letters, vol. 14, No. 2 (Feb. 1987), pp. 139-142.

* cited by examiner

*Primary Examiner*—Eric F. Winakur
*Assistant Examiner*—Jack Lin
(74) *Attorney, Agent, or Firm*—Reed Smith LLP; Stanley P. Fisher, Esq.; Juan Carlos A. Marquez, Esq.

(57) ABSTRACT

An image generating methodology for displaying brain activation areas with improved accuracy in a living body light measurement system for generating an image of the changes in blood volume of the brain. A spatial intensity distribution of changes in blood volume can be generated by detecting brain activation in many sampling points, and a spatial interpolation process is executed on this data. A threshold process is executed on the distribution to extract the distribution of coordinates having a signal intensity of at least the predetermined threshold. The displacement between the brain activation area and the maximal location of the distribution is stored in a recording unit of the system in order to compensate for the distribution extracted by the threshold process. Accordingly, brain activation areas can be estimated with greater location accuracy, and the diagnosis and medial treatment for brain diseases can likewise be executed with greater accuracy.

14 Claims, 21 Drawing Sheets

FIG. 5
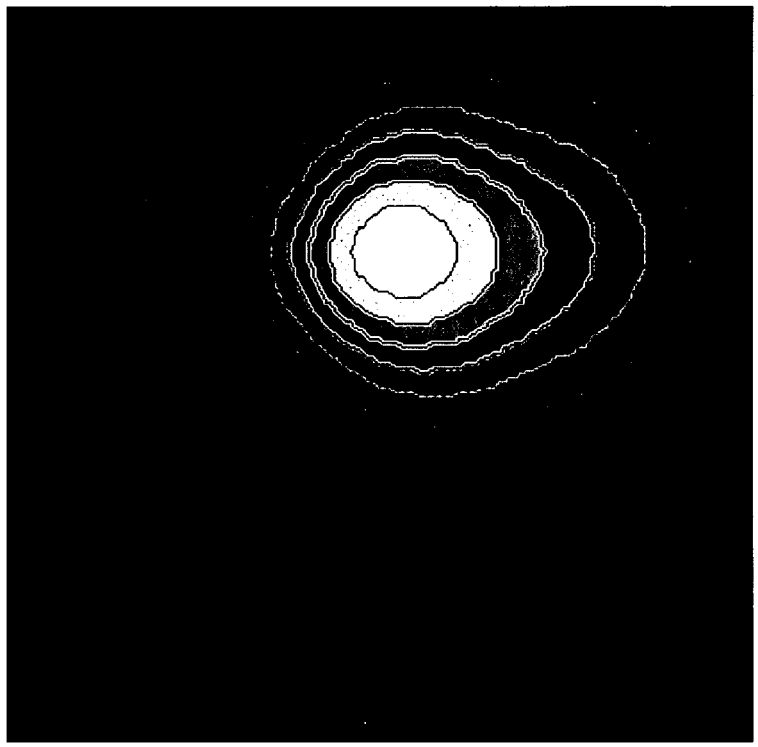
BLOOD VOLUME
INCREASE
DECREASE

LIVING BODY LIGHT MEASUREMENT SYSTEM AND SIGNAL PROCESSING METHOD

CLAIM OF PRIORITY

The present application claims the benefit under 35 U.S.C. § 119 of the earlier filing date of Japanese Patent Application JP 2004-050741 which was filed on Feb. 26, 2004, the content of which is hereby incorporated by reference into the present application.

BACKGROUND OF THE INVENTION

1. Field of the Invention

The present invention relates to a living body light measurement system, and, more particularly, the present invention is directed to a method for displaying images indicating a special distribution of changes in concentration and a method for displaying such images in a living body light measurement system capable of measuring the concentration of metabolic substances of a living body or the changes in the concentration using the light of the living body.

2. Description of the Background

Diagnosis of diseases in the brain can be realized by measuring, when possible, the activation of the human brain. Moreover, recovery processes and the monitoring of rehabilitation of these diagnosed brain diseases may also be realized. Therefore, various measuring systems for brain functions have been proposed.

In recent years, a practical brain activation measuring system introducing the near infrared spectral method has been proposed. Near infrared rays have a higher transmitting property for living body tissues compared to other light beams in various wavelengths (colors). Therefore, changes in blood volume at the cortex existing at the internal side of the skull can be measured. In addition, it is possible to obtain dynamic images of the changes in blood volume resulting from activation of the brain by measuring such changes at multiple locations (i.e., at multiple points). A summary of such multiple-channel light brain function measuring system has been described in Atsushi Maki, et al., "Spatial and temporal analysis of human motor activity", Medical Physics, Vol. 22 (No. 12), pp. 1997–2005 (1995) (hereafter, "Non-Patent Document 1"). The measuring technology published by this document will be described below.

FIG. 2 illustrates the structure of a system to perform the measurement disclosed in Non-Patent Document 1 or a similar process. A subject (2-1) wears a helmet (i.e., probe) (2-2) before beginning the measurement. The probe 2-2 is alternately provided with a light illumination location in which optical fibers (S11 to S18) connected to a light source are placed and a light detection location in which optical fibers (D11 to D18) connected to a light detector are placed with interval of about 30 mm. The optical fibers connected to the light source (S11 to S18) are respectively connected to double-wavelength lasers (2-3-1 to 2-3-8 and 2-4-1 to 2-4-8) in different wavelengths. In Non-Patent Document 1, the light sources used are about 780 nm and 830 nm, around the wavelength of 800 nm, wherein the molecule extinction coefficients of oxygenation hemoglobin and de-oxygenation hemoglobin become identical.

Moreover, in FIG. 2, the light illuminated from the optical fiber S13 is detected with the optical fibers D13, D11, D15, D14 which are isolated by 30 mm from the place of the optical fiber S13. The light having reached the optical fibers for detection D11 to D18 are detected with a light detector 2-6 (semiconductor light detector, e.g., an avalanche photodiode, photomultiplier or similar device). The detected light is processed with a control and process device 2-5. A blood volume which has been changed at the cortex in accordance with the activation of the brain can be calculated on the basis of the result of processing the light at each light illumination location and each light detection location (provided alternately at intervals of 30 mm). The result of this calculation is displayed on an electronic computer including a display as waveform (time domain) and an image showing the activations (i.e., activity) of the brain.

FIG. 3 illustrates a method of measuring changes in blood volume in accordance with activations (i.e., activities) of the brain. In this figure, a propagation path (3-5) of light being propagated between a holder (3-2) for fixing an optical fiber (3-1) connected to a light source and a holder (3-4) for fixing an optical fiber (3-3) connected to a light detector. Each holder fixes an optical fiber using a screw 3-6. These holders are fixed with a resin 3-7 which also forms the helmet (2-2). As a result, the end part of the optical fiber is placed in contact with the scalp of the subject 3-8.

In FIG. 3, a typical structure of the brain of a human is also illustrated. The brain is generally formed, in addition to the scalp 3-8 described above, of the skull 3-9, cerebrospinal fluid layer 3-10, and cortex 3-11, or the like. Here, it is known that these living body tissues have known optical scattering characteristics and absorbing characteristics and that the optical scattering characteristic of the skull is particularly large.

Therefore, it is also known that the light illuminated from the light source is scattered depending on the optical scattering characteristic and is gradually lost in the intensity thereof depending on the optical absorbing characteristic. Here, the holders illustrated in the figure are located with the intervals of about 30 mm. Moreover, it is known that under this allocation interval, the light illuminated from the optical fiber 3-1 connected to the light source is propagated through the living body tissues in an arc shape 3-5 (like a banana) as illustrated and is then detected after the light has reached the optical fiber 3-3 connected to the light detector. In this figure, 3-12 illustrates the area where the blood volume increases in accordance with activation of the brain. For example, when the blood volume increases, intensity (I) of the light having reached the optical fiber for detection 3-3 is reduced.

Therefore, a change in the light absorption degree (ΔA: corresponding to a logarithmic difference value of the detected light intensity before and after activation of the brain) due to a change in the concentration of oxygenation hemoglobin and de-oxygenation hemoglobin (ΔCoxy, ΔCdeoxy) can be established as follows (equation (1)) for each wavelength λ used for measurement (λ1=780 nm and λ2=830 nm in Non-Patent Document 1):

$$\Delta A = -\ln(I_1/I_0) = \epsilon_{oxy}\Delta C_{oxy}L + \epsilon_{deoxy}\Delta C_{deoxy}L \quad (1)$$

Here, L in equation (1) denotes an average optical propagation path length between the light source and the light detector. Moreover, $\epsilon$oxy and $\epsilon$deoxy in equation (1) denote respectively the molecule extinction coefficients of oxygenation hemoglobin and de-oxygenation hemoglobin. Also in equation (1), I denotes the intensity of light arriving at the detector and $I_0$ and $I_1$ represent the intensity of light before activation of the brain and during activation of the brain, respectively. Changes in concentration (ΔCoxy, ΔCdeoxy) of oxygenation hemoglobin and de-oxygenation hemoglobin due to the activation of brain can be expressed as equation (2) by applying equation (1) to each wavelength:

$$\begin{pmatrix} \Delta C_{oxy} \\ \Delta C_{deoxy} \end{pmatrix} = \begin{pmatrix} \varepsilon_{oxy}^{\lambda 1} & \varepsilon_{deoxy}^{\lambda 1} \\ \varepsilon_{oxy}^{\lambda 2} & \varepsilon_{deoxy}^{\lambda 2} \end{pmatrix}^{-1} \begin{pmatrix} \dfrac{-\ln(I_1^{\lambda 1}/I_0^{\lambda 1})}{L^{\lambda 1}} \\ \dfrac{-\ln(I_1^{\lambda 2}/I_0^{\lambda 2})}{L^{\lambda 2}} \end{pmatrix} \quad (2)$$

However, since it is difficult to actually determine the value of L, equation (3) may be used:

$$\begin{pmatrix} \Delta C'_{oxy} \\ \Delta C'_{deoxy} \end{pmatrix} = L \begin{pmatrix} \Delta C_{oxy} \\ \Delta C_{deoxy} \end{pmatrix} \quad (3)$$

Where C', which is a unit having the dimension wherein concentration is multiplied with distance, can be calculated as follows:

$$\begin{pmatrix} \Delta C'_{oxy} \\ \Delta C'_{deoxy} \end{pmatrix} = \begin{pmatrix} \varepsilon_{oxy\lambda 1} & \varepsilon_{deoxy\lambda 1} \\ \varepsilon_{oxy\lambda 2} & \varepsilon_{deoxy\lambda 2} \end{pmatrix}^{-1} \begin{pmatrix} -\ln(I_{1\lambda_1}/I_{0\lambda_1}) \\ -\ln(I_{1\lambda_2}/I_{0\lambda_2}) \end{pmatrix} \quad (4)$$

Next, a method for imaging the result of the above calculations will be described with reference to FIG. 4 and FIG. 5. FIG. 4 illustrates a sensor locating method for the condition that eight light illumination locations for the optical fibers S11 to S18 connected to the light source and eight light detection locations for the optical fibers D11 to D18 are respectively allocated on the scalp of the subject. The eight white squares (□, 4-1) and eight black squares (■, 4-2) indicate the light illumination points and light detection points, respectively. Moreover, the locations (4-3) indicated by the black circles are located almost at the intermediate locations between the light illumination location and the light detection location. These intermediate locations are defined as the sampling points giving the location information of change in blood volume detected from a change in the intensity of the light having reached the light detection location after illumination from the light illumination location. The reason why the sampling point has been established as an almost intermediate point between the two fibers will be described using the light propagation path 3-5 illustrated in FIG. 3. According to this light propagation path, the light is not propagated to the areas just under the light illumination locations 4-1 and light detection locations 4-2.

Moreover, at the area just under the intermediate point between the light illumination location 4-1 and light detection location 4-2, the light is propagated not only to the skull but also to the cerebrospinal fluid layer and the cortex as the brain activation area. Since the area considered as the actual brain activation area is the cortex, according to the light propagation characteristic illustrated in FIG. 4, a change in the blood volume detected by a pair of light source and light detector may be assumed to become a maximum when change in the blood volume is changed at the area just under the intermediate point of the light illumination location and the light detection location. Therefore, the intermediate point 4-3 between the light illumination location 4-1 and light detection location 4-2 is defined as the sampling point and also as the point giving the location information of change in blood volume detected by using a pair of light source and light detector. In the allocation method of the light source and light detector illustrated in FIG. 4, 24 sampling points are provided keeping the intervals of 21 mm (which is equal to $\sqrt{(1/2)}$ times the sensor allocation interval of 30 mm).

As an example, a topographic image illustrated in FIG. 5 can be obtained by spatially interpolating the change in blood volume of the measuring area enclosed by these 24 sampling points. The areas where the change in blood volume is large can be detected by displaying a change in blood volume using contour lines and concentration lines or a similar methodology.

In FIG. 5, the areas where the change in blood volume is large are indicated as the brighter (lighter) area, while the areas where change in blood volume is small are indicated as the darker areas. The "topography" referred to in this topographic image means a "topographical map" and a space distribution of the physical amount of the dimension which is different from that of the location information on a plane is displayed on this plane. For a description of this specification, a coordinate is established in FIG. 4. This coordinate includes the x-y axes, and the origin is established at the center of the measuring areas. Therefore, x and y change in the areas of $-45 \leq x$, $y \leq 45$ and the measuring areas is extended up to 90×90 mm².

In addition to Non-Patent Document 1 described above, some comments on the following additional references with be provided below: E. Watanabe, et al., "Noninvasive Cerebral Blood Volume Measurement During Seizures Using Multi-channel Near Infrared Spectroscopic Topography", Journal of Biomedical Optics, 2000, July, 5(3), P. 287–290 ("Non-Patent Document 2"); E. Watanabe, et al., "Noninvasive assessment of language dominance with Near-Infrared Spectroscopic mapping", Neurosci. Lett. 256 (1998) ("Non-Patent Document 3"); T. Yamamoto, et al., "Arranging optical fibers for the spatial resolution improvement of topographical images", Phys. Med. Biol. 47 (2002) ("Non-Patent Document 4"); and Sandwell, David T., "Biharmonic Spline Interpolation of GEOS-3 and SEASAT Altimeter Data", Geophysical Research Letters, 2, 139–142, 1987 ("Non-Patent Document 5").

The topographic image illustrated in FIG. 5 is displayed under the condition that a change in blood volume is blurred. Meanwhile, such blur is rather small in the image of brain activation picked up with a functional magnetic-resonance imaging system or a positron topographic imaging system which are conventional brain function measurement systems. This is because the spatial distribution of the sampling points in the light topography method is somewhat smaller than that in the other brain function measurement systems. In the multi-channel brain function measurement system illustrated in FIG. 2, measurement is conducted by placing the optical fiber used for the measurement in contact with the scalp of the subject. At the time of generating a topographic image, the location information of a change in blood volume detected with a pair of sensors is given by establishing the intermediate point of the optical fiber location connected to the light source and detector as the sampling point.

Accordingly, unless the number of optical fibers used for measurement is increased, it is impossible to increase the spatial location density at the sampling points. However, the ability to increase the number of optical fibers is limited because the number of optical fibers gives influence on the structure of the helmet. Meanwhile, since the functional magnetic-resonance imaging system and the positron topographic imaging system are used for non-contact measurement in which the sensors are never placed in contact with the subject, the sampling points can be established in principle without any limitation. Since changes in blood volume can be measured in the multiple points, blurring of the images is somewhat small in comparison with the topographical images.

On the other hand, even when the spatial resolution is lower than that of the functional magnetic-resonance imaging system or positron topographic imaging system, a multi-channel light brain function measurement system illustrated in FIG. 2 may be used in the actual medical field. For example, the Non-Patent Documents 2 and 3 disclose that such a system is presently used for identifying the location of neurotic epilepsy and language dominance. On the basis of such documents, users estimate the activation areas from the spatial distribution of changes in blood volume displayed with the topographic images. Therefore, the accurate display of the activation areas of the brain is needed as a tool for identifying the locations of neurotic epilepsy and language dominance.

Accordingly, in order to evaluate the location accuracy of a topographic image based on the present topographic image creating algorithm and to determine the topographic image creating algorithm to obtain still higher location accuracy from the results of such an evaluation, the location accuracy of a topographical image has been evaluated using computer simulation. A simulation model is illustrated in FIG. 6. As illustrated in this figure, the structure of a human brain is modeled in a three-layer structure formed of skull 6-1, cerebrospinal fluid layer 6-2, and cortex 6-3. Such a model structure is widely used even in the documents which have already been made public. For example, this structure is described in Non-Patent Document 4. Moreover, the area 6-4 indicates a location of the brain activation area existing over the cortex.

The method for assessing the location accuracy using the model illustrated in FIG. 6 will be described with reference to FIG. 7 through FIG. 9. FIG. 7 illustrates an allocation where an optical fiber 7-1 for illumination and a fiber 7-2 for detection are placed in contact with the upper side of brain model illustrated in FIG. 6. Here, it is preferable that these two optical fibers be located with an interval of 30 mm. It is known, from Non-Patent Document 4, that the spatial distribution (sensitivity distribution) of $\Delta A$ in equation (1) when the brain activation area is changed and the light absorbing coefficient at the brain activation area is also changed for the locations of these optical fibers in locations of these optical fibers, shows the elliptical shape distribution as illustrated at the lower portion of FIG. 8. Here, the location of an optical fiber for illumination 8-1 and an optical fiber for detection 8-2 are designated.

For a qualitative expression of this elliptical shape, the spatial distribution of $\Delta A$ is expressed using the function of equation (5) given below. Here, $\Delta x$, $\Delta y$ indicates the half-value widths in the directions of the x axis and y axis. Typically, $\Delta x$ is known to take a value in the range of 20 to 40 mm, while $\Delta y$ is known to take a value in the range of 10 to 30 mm.

$$\Delta A(x, y) = \exp^{-\frac{x^2}{\Delta x^2}} \exp^{-\frac{y^2}{\Delta y^2}} \quad (5)$$

FIG. 9 illustrates an allocation method of a light source and a light detector used for generation of a topographic image. 9-1 designates the location of light illumination to a light source represented by a laser or a light emitting diode. 9-2 designates the location of a light detector such as an avalanche photodiode or a photomultiplier. As illustrated in FIG. 8, since the sensitivity of $\Delta A$ at the intermediate point of the locations between the light source and light detector shows as a maximum, this intermediate point is defined as the sampling point 9-3 and as the point which gives the location information of a change in the blood volume detected with a pair of light source 9-1 and light detector 9-2. In FIG. 9, 24 sampling points are provided.

The brain activation area is established in the area enclosed by the light source, light detector, and sampling points, and a topographic image can be generated using the spatial distribution of the sensitivity given by FIG. 8 and equation (5). Therefore, a method of assessing the location accuracy will be described by referring to FIG. 10. The brain activation area 10-3 indicated as 6-4 in FIG. 6 is established for eight light illumination points 10-1 and eight light detection points 10-2 at the upper side of the skull (FIG. 10A). The central location of the brain activation area is defined as (Xc, Yc). A change in the degree of light absorption at the 24 sampling points 10-4 is obtained with the computer simulation for this brain activation area. The distribution of the changes in light absorption degree is then visualized as a topographic image 10-5 (FIG. 10B). The maximum point which is of the most interest to users of the system among the topographic image is defined as (Xmax, Ymax), and this maximum point has been obtained.

More concretely, the values of $\Delta A$ detected with the 24 pairs of light sources and light detectors existing in FIG. 10 are calculated as the value of $\Delta A$ at the 24 sampling points using equation (5) for changes in light absorption degree at the central location (Xc, Yc) of the preset brain activation (S1-1 in FIG. 21). A topographic image can be visualized (S1-2 in FIG. 21) with the spatial interpolation process using the value of each $\Delta A$. The location information for obtaining such $\Delta A$ and the maximum location (Xmax, Ymax) thereof has been obtained (S1-3 in FIG. 21). The interpolation process has been executed in this embodiment with the method (inverse distance method) described in Non-Patent Document 5.

Displacement can be detected by comparing the central location (Xc, Yc) of the brain activation area and the maximum location (Xmax, Ymax) of the topographic image. Such displacement is generated because the interpolation is executed using $\Delta A$ at each sampling point and the location coordinate thereof in order to generate a topographic image with the spatial interpolation. The topographic image intensity reflects the location information at each sampling point.

The maximum point (Xmax, Ymax) for the central point (Xc, Yc) obtained by simulation is expressed with vectors (S1-4 in FIG. 21) and the resulting obtained distribution is illustrated in FIG. 11. Moreover, the flowchart for obtaining distribution of the displacement information is illustrated in FIG. 21.

FIG. 11A shows light illumination points 11-1; light detection points 11-2; and sampling points 11-3. In this figure, the point (Xc, Yc) is ranged as $-15 \leq (Xc, Yc) \leq 15$ and the point (Xmax, Ymax) for the each point (Xc, Yc) within this range has been obtained. In FIG. 11B, the starting point of each vector is (Xc, Yc) and the end point thereof corresponds to (Xmax, Ymax), showing the displacement of the topographic image. This result suggests that the displacement of the topographic image shows the following trends:

(1) When the brain activation area is visualized with a topographic image, the topographic image is displayed with displacement toward the sampling point which is nearest to the center of the brain activation area.

(2) When the topographic image is displayed with a certain displacement toward the sampling point, this topographic image is never displayed over the sampling points.

(3) At the central point (Xc1, Yc1) of a certain brain activation area and a point (Xc2, Yc2) which is farther from the sampling point than a point (Xc1, Yc1), a displacement toward the sampling point becomes larger in the point (Xc2, Yc2).

Here, the actual brain is different among different individuals in many parameters. For example, different people will have different: thicknesses of each skull, cerebrospinal fluid, and/or cortex layer illustrated in FIG. 6; scattering coefficient characteristics for the scattering of light, light absorbing coefficient characteristics for the absorption of light, sizes of activation areas, and changes in the light absorbing coefficient due to brain activation. Therefore, it is necessary to check whether the trends in displacement of the topographic image described in the items (1) to (3) are usually generated among the individuals or not. However, it is difficult to realize the simulation by changing all of the numerous parameters.

Accordingly, while the effects, which are similar to that in the simulation in which numerous parameters are changed, are obtained, a more simplified simulation can be realized by conducting the simulation through changes of the values of $\Delta x$ and $\Delta y$ in the elliptic function of the equation (5). The reason is that these are values depending on the parameters. As a result of simulation through changes of the values of $\Delta x$ and $\Delta y$, it has been confirmed that the trends in displacement of the topographic image described in the items (1) through (3) are never changed even when the values of $\Delta x$ and $\Delta y$ are changed.

Namely, it has been confirmed that the trends of such displacement never change among the individuals (difference in thickness or other characteristics of the skull, cerebrospinal fluid layer, cortex) and these changes occur in general.

SUMMARY OF THE INVENTION

An object of the present invention is therefore to provide a method of compensating for topographic images using the distribution illustrated in FIG. 11.

A spatial intensity distribution of the changes in blood volume is generated by detecting brain activation at many sampling points distributed on the scalp of the subject and then conducting spatial compensation. A signal intensity distribution of the coordinate having signal intensity which is higher than the predetermined threshold is extracted by performing the threshold process to this signal intensity distribution. The information about displacement between the brain activation area generated when the signal intensity distribution is generated and the maximum area of the signal intensity distribution is previously stored to a computer (recording unit) of a living body measurement system, and the signal intensity distribution extracted by the threshold process is compensated by referring to the displacement information stored therein.

Since the brain activation area can be estimated with a location accuracy which is higher than the conventionally achieved accuracy, diagnosis for the diseased areas of the brain and medical treatments based on the results of these diagnoses can be realized with improved accuracy.

BRIEF DESCRIPTION OF THE DRAWINGS

For the present invention to be clearly understood and readily practiced, the present invention will be described in conjunction with the following figures, wherein like reference characters designate the same or similar elements, which figures are incorporated into and constitute a part of the specification, wherein:

FIG. 5 is a diagram illustrating an exemplary topographic image including a brain activation area;

DETAILED DESCRIPTION OF THE INVENTION

Figure 2:
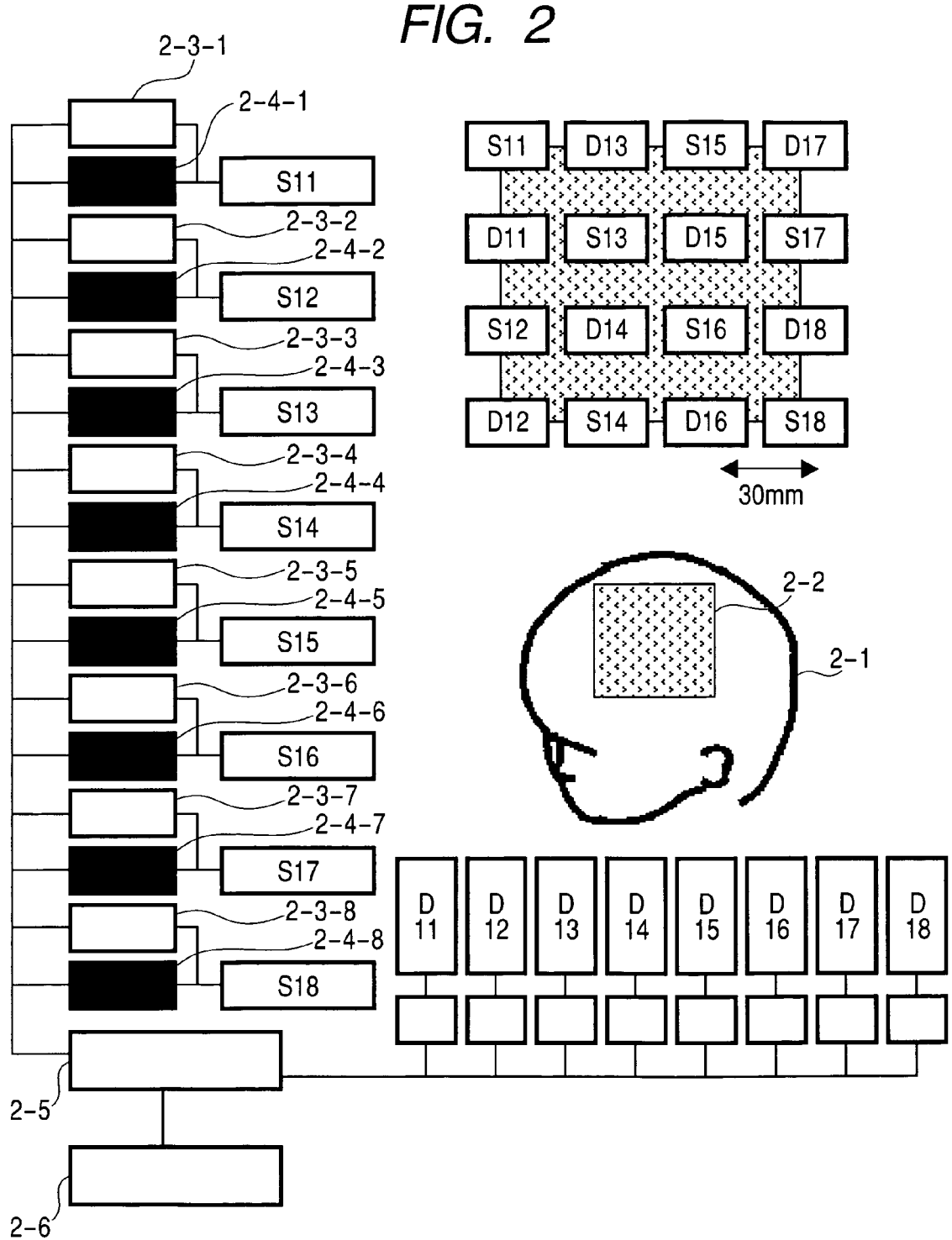
FIG. 2 is a schematic diagram of a conventional multi-channel light brain function measurement system.
Figure 3:
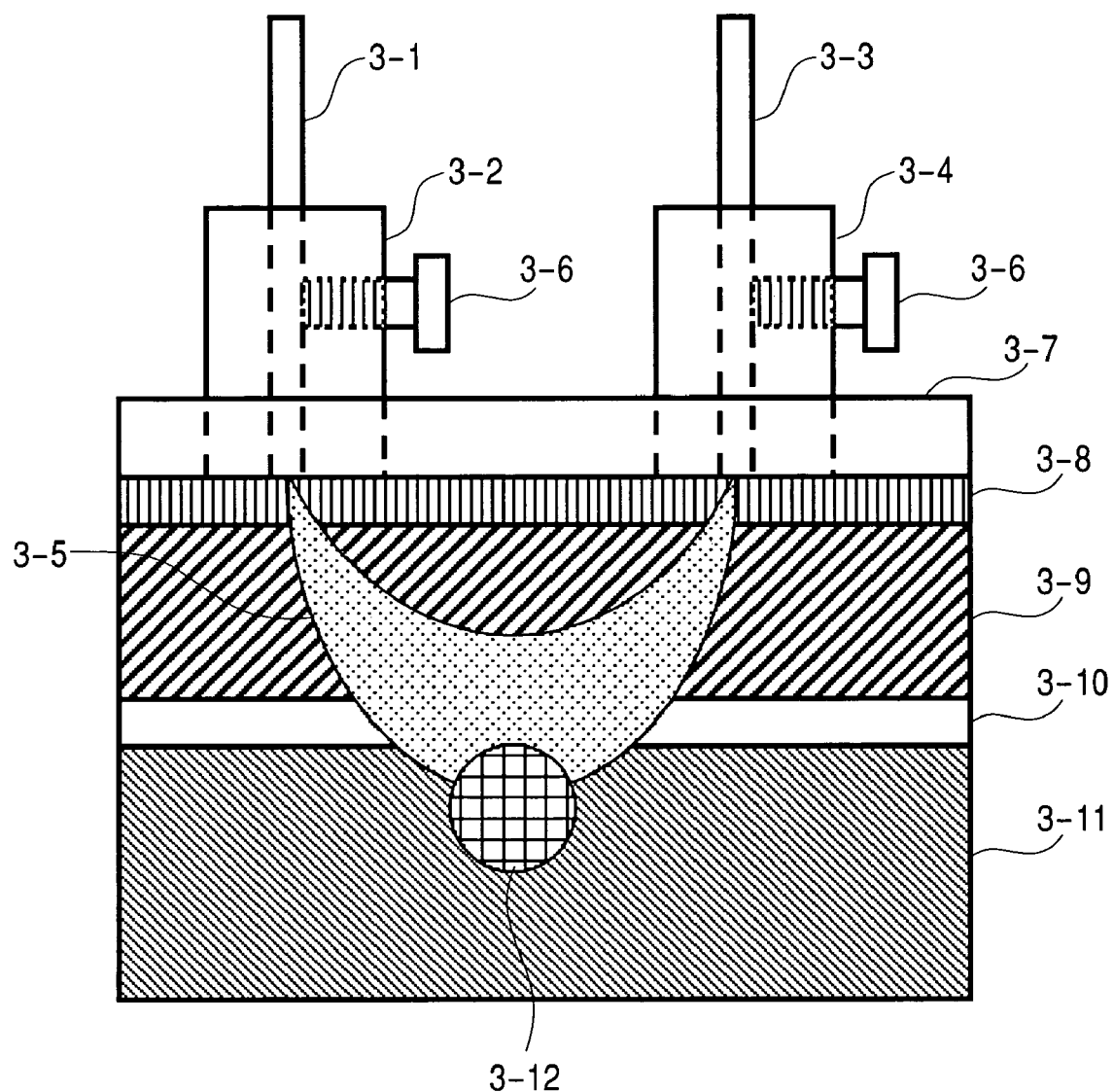
FIG. 3 is a diagram illustrating a method of measuring the change in blood volume due to brain activation.
Figure 11A:
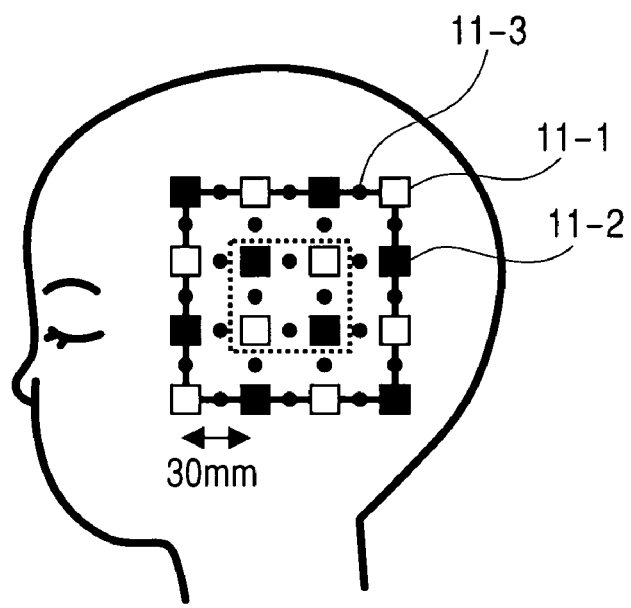
FIG. 11 is a diagram illustrating the distribution of displacements obtained from the computer simulation, including a spatial diagram (FIG. 11A) and a vector map (FIG. 11B)
Figure 11B:
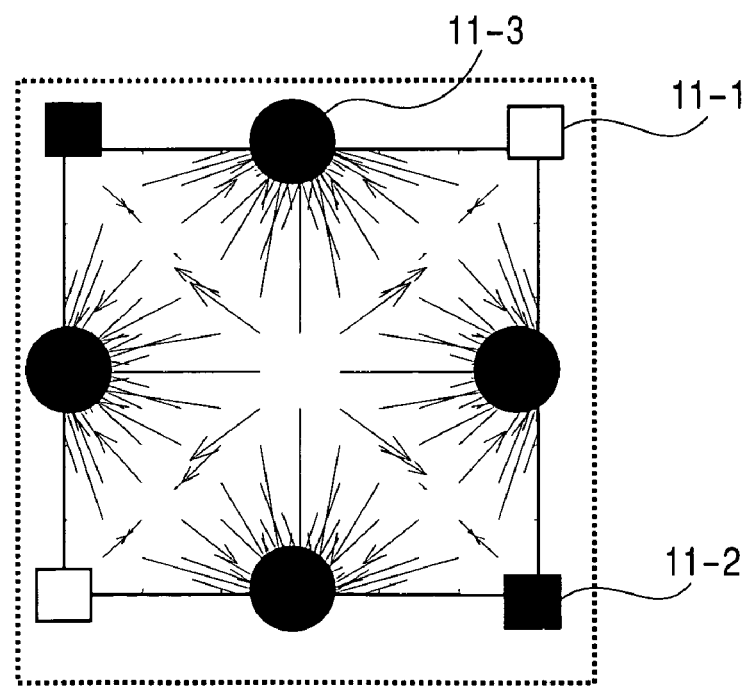

In a first preferred embodiment of the present invention, a distribution of displacements illustrated in FIG. 11 is initially stored directly within a storage device (e.g., a memory or hard disk drive) provided in a computer 2-5 which includes a display illustrated in FIG. 2. Moreover, this distribution may also be stored in a storage device in the computer 2-5 using an information storage medium such as a CD-ROM.

The present invention includes several methods of compensating for the distribution of displacements illustrated in FIG. 11 and the results obtained from testing various methods are provided herein.

Figure 4:
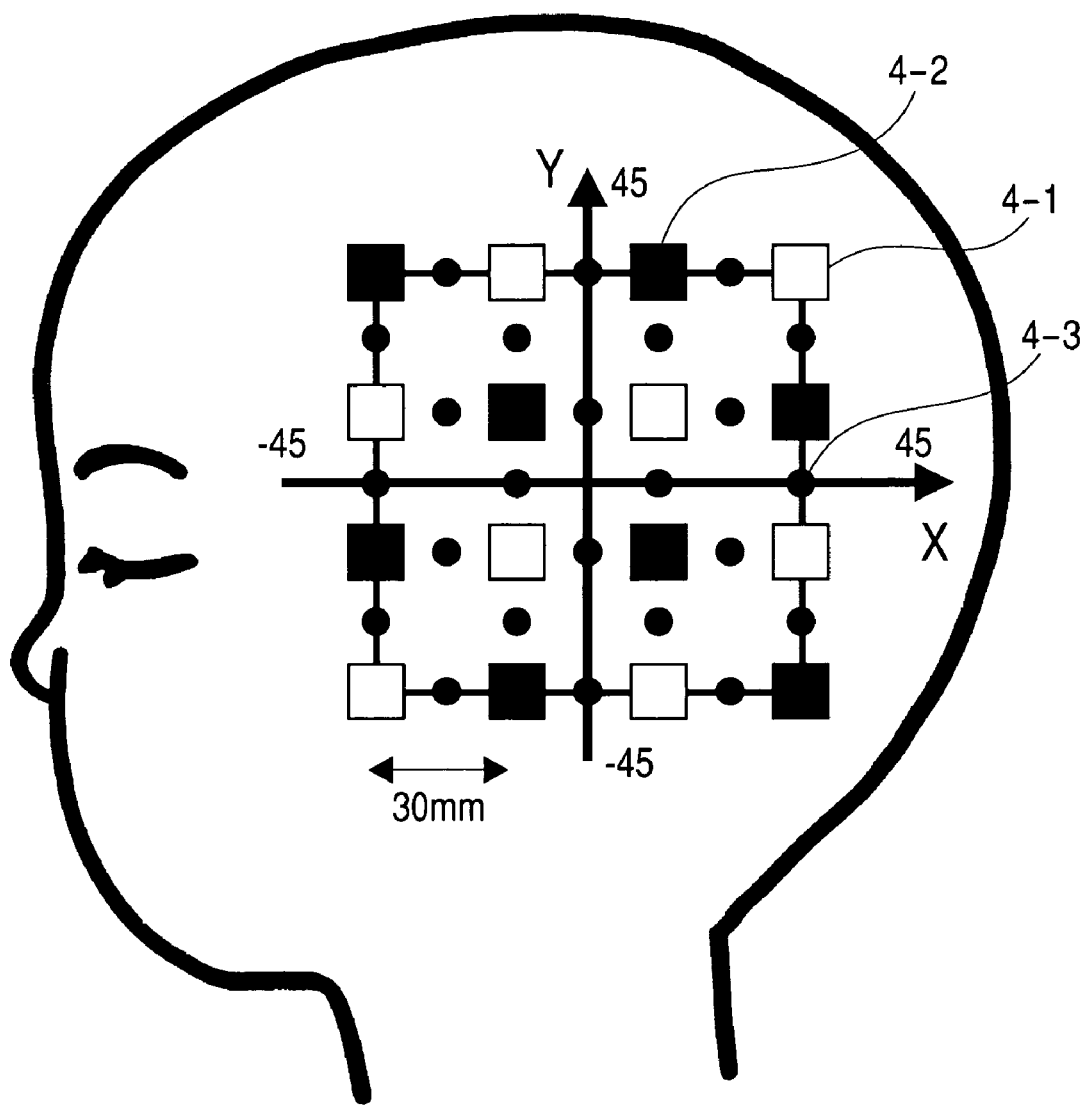
FIG. 4 is a diagram illustrating a method for locating light sources and light detectors for generating topographic images.
Figure 6:
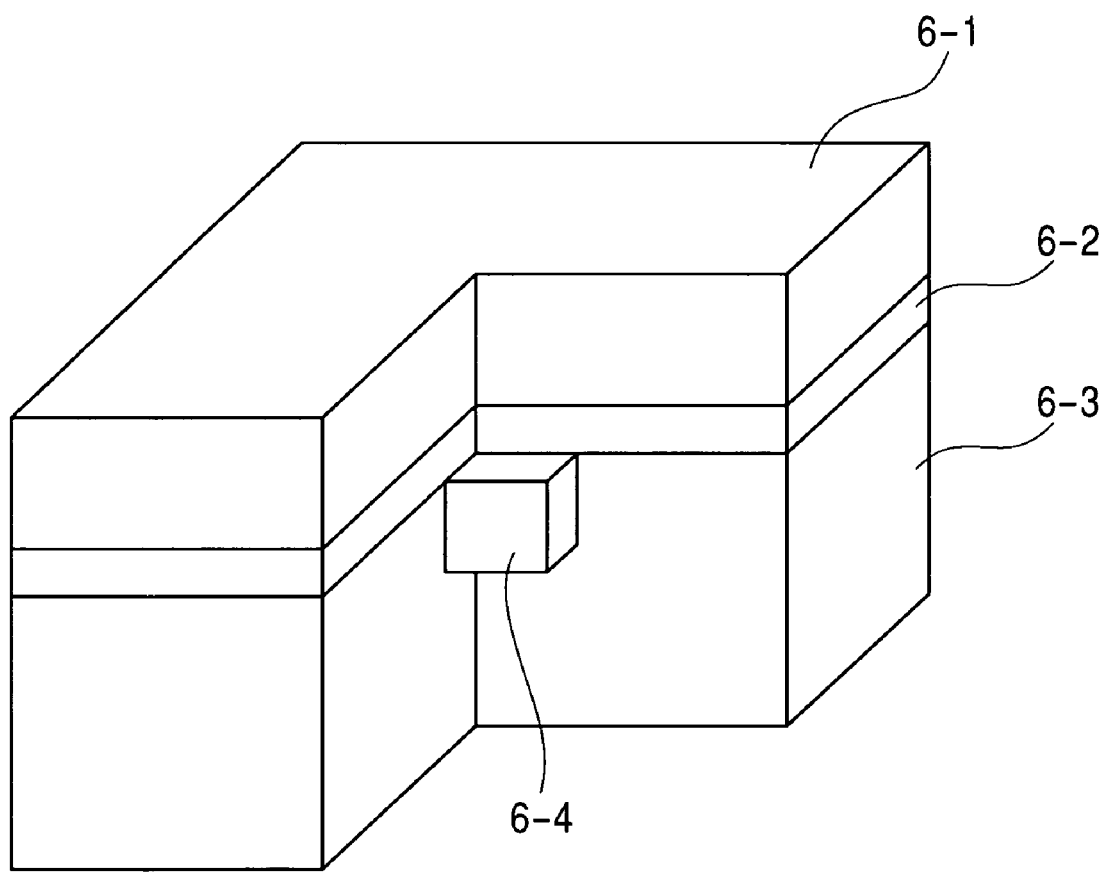
FIG. 6 is a diagram illustrating a simulation model of a brain structure.
Figure 7:
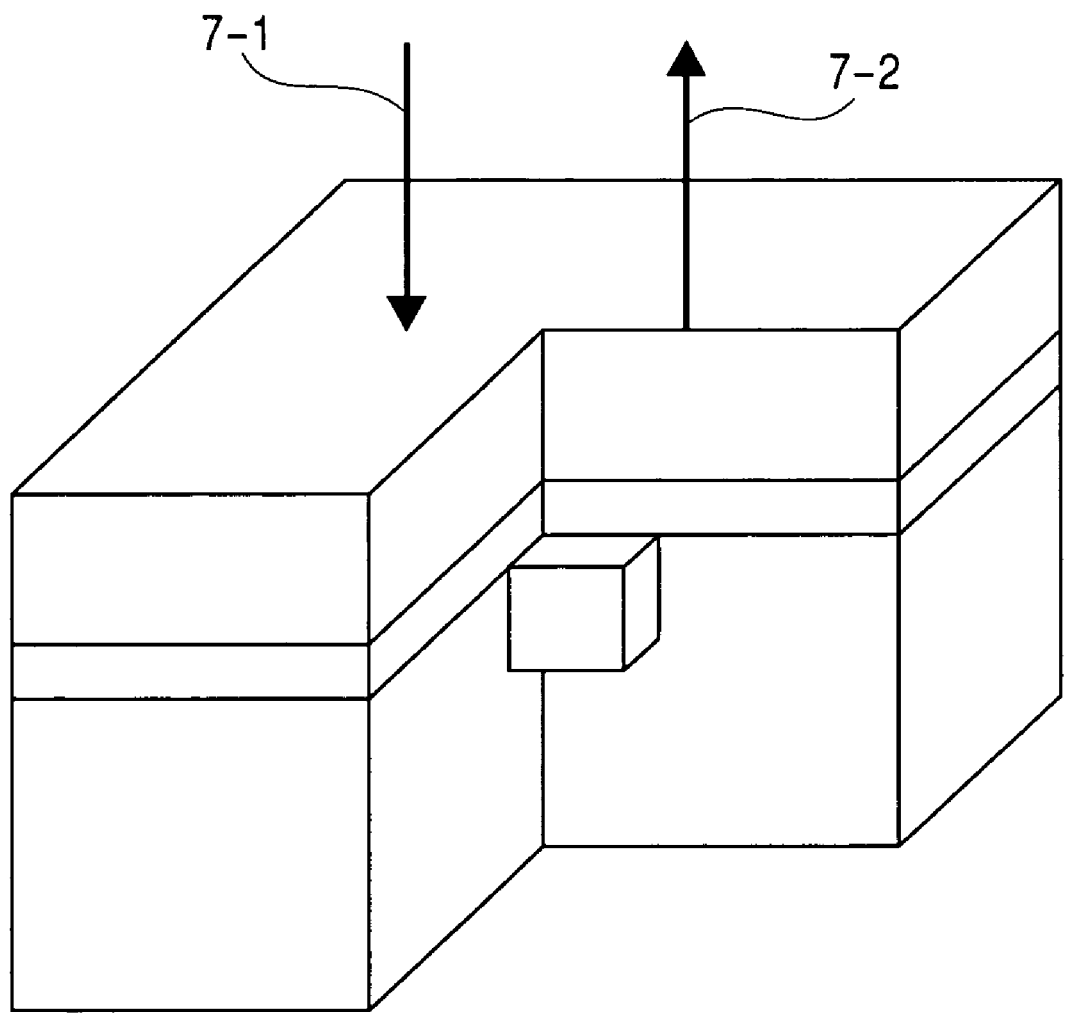
FIG. 7 is a diagram illustrating a method of assessing the sensitivity distribution of the model of FIG. 6.
Figure 12:
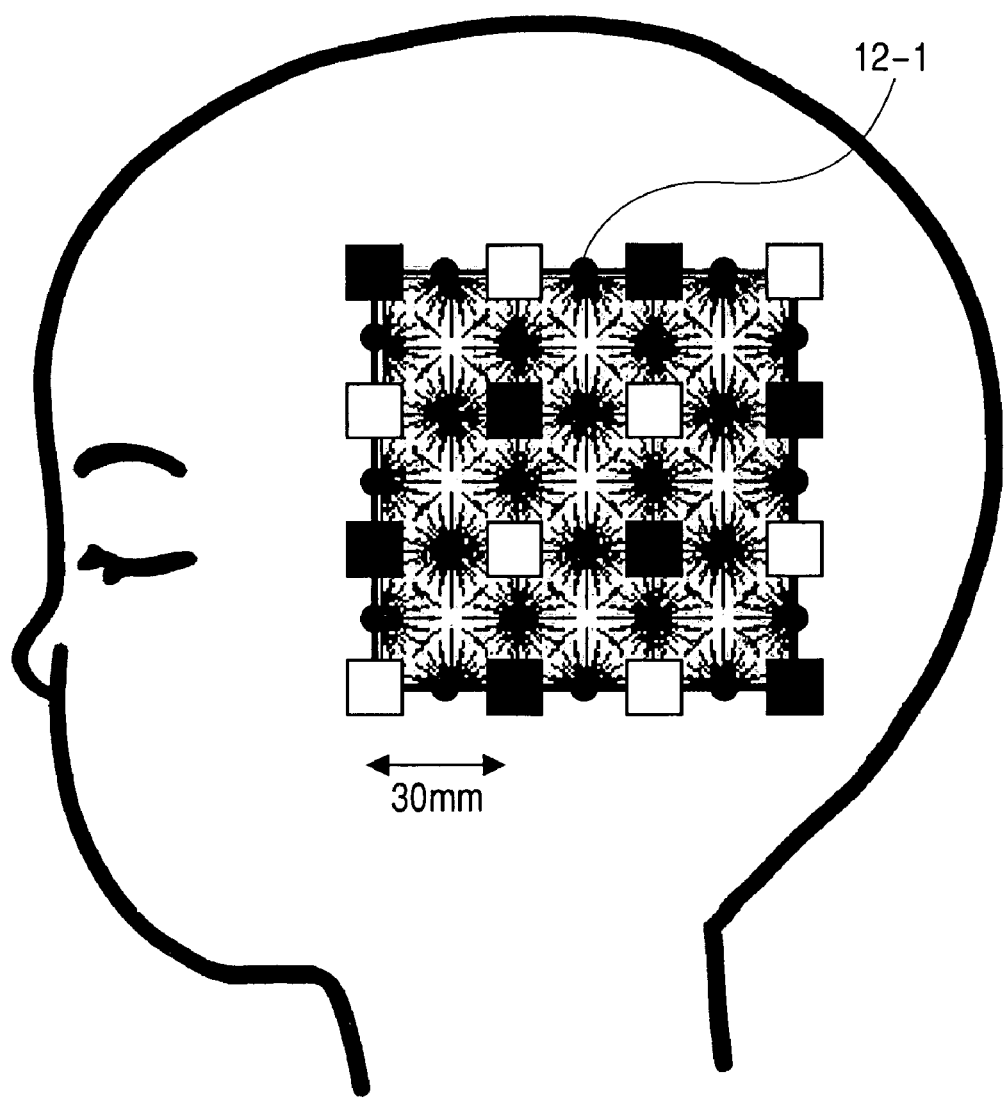
FIG. 12 is a diagram illustrating an image of distribution of displacements for an entire part of the measurement area illustrated in FIG. 11.
Figure 13:
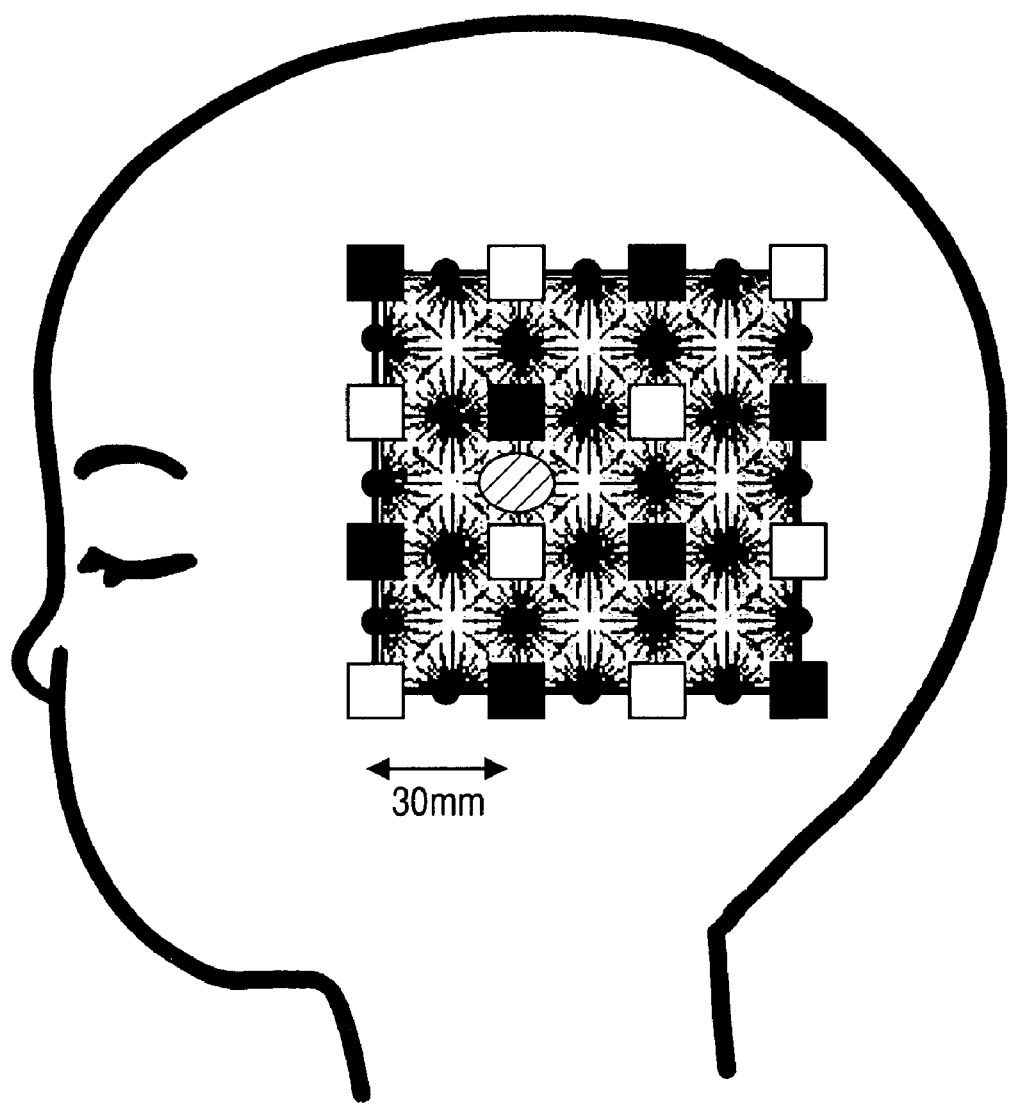
FIG. 13 is a diagram where the topographic images are adhered to the distribution of displacements illustrated in FIG. 12.

In a first method, pixels of a topographic image which are spatially distributed are compensated in accordance with distribution of displacements illustrated in FIG. 11. Validity of this method will be discussed with reference to FIG. 12, FIG. 13, and FIG. 14. FIG. 12 illustrates the visualized distribution of displacements of FIG. 11 obtained for the entire part of a measurement area. As is apparent from this figure, it is understood that a topographic image is displayed through attraction toward the sampling point 12-1 which is nearest to the central point of the brain activation area. FIG. 13 is a diagram where an example of the topographic image indicating the brain activation is adhered to the distribution of displacements of FIG. 12. When the topographic image is adhered, the figure is rather complicated. Therefore, the topographic image is converted to a binary data image, discriminating the hatched area (the central point thereof exists at (Xc, Yc)=(-15, 0) in FIG. 4) and the non-hatched area.

Figure 14:
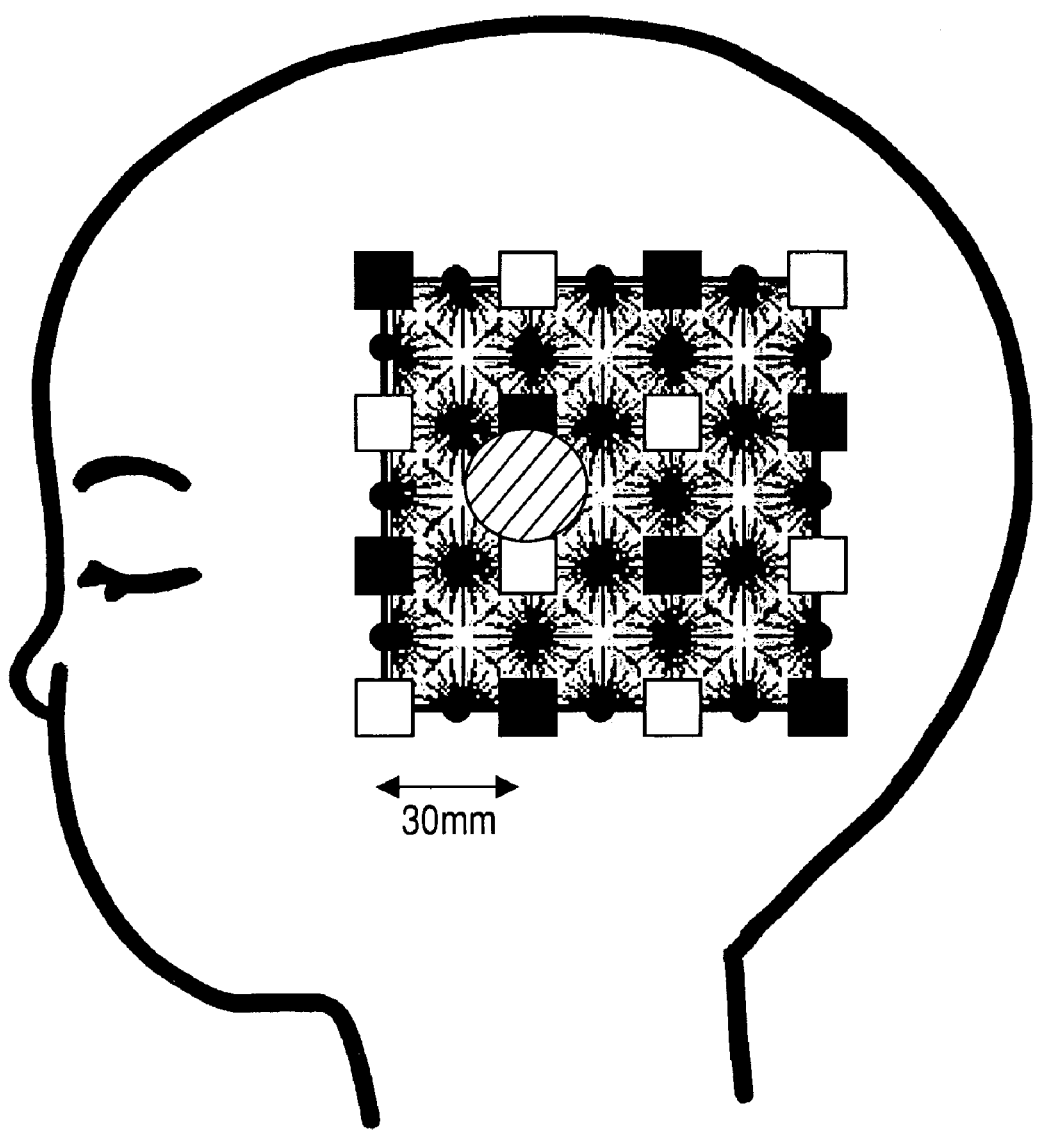
FIG. 14 is a diagram illustrating a topographic image where the compensation process is performed on the basis of a first algorithm to FIG. 13.

The results of compensation for the topographic image illustrated in FIG. 13 based on the method for compensation for the spatially distributed pixels of topographic image in accordance with the distribution of displacements of FIG. 11 are illustrated in FIG. 14. According to FIG. 14, it is shown that the topographic image which is expanded in comparison with the original image of FIG. 13 is displayed. The cause of this expansion will be described with consideration of the distribution of displacements of FIG. 12. From the distribution of displacements, it can be understood that the topographic image is displaced toward the nearest sampling point. From the inverted point of view of this result, it is shown that when the topographic image displayed at the point nearest to the sampling point is compensated, the topographic image is displayed at a point which is far from the sampling point.

Therefore, if the compensation process is implemented to the topographic image, which is displayed in the manner that the central area of the brain activation area exists at the area near the sampling point and the image is spreading for display to the area near the central point as in the topographic image of FIG. 13, the image is further spread, resulting in a deterioration in the image quality. Accordingly, an algorithm for compensating for the pixels of the topographic image which are spatially distributed in accordance with the distribution of displacements of FIG. 11 is considered to have lower validity than other methods discussed herein.

Figure 8:
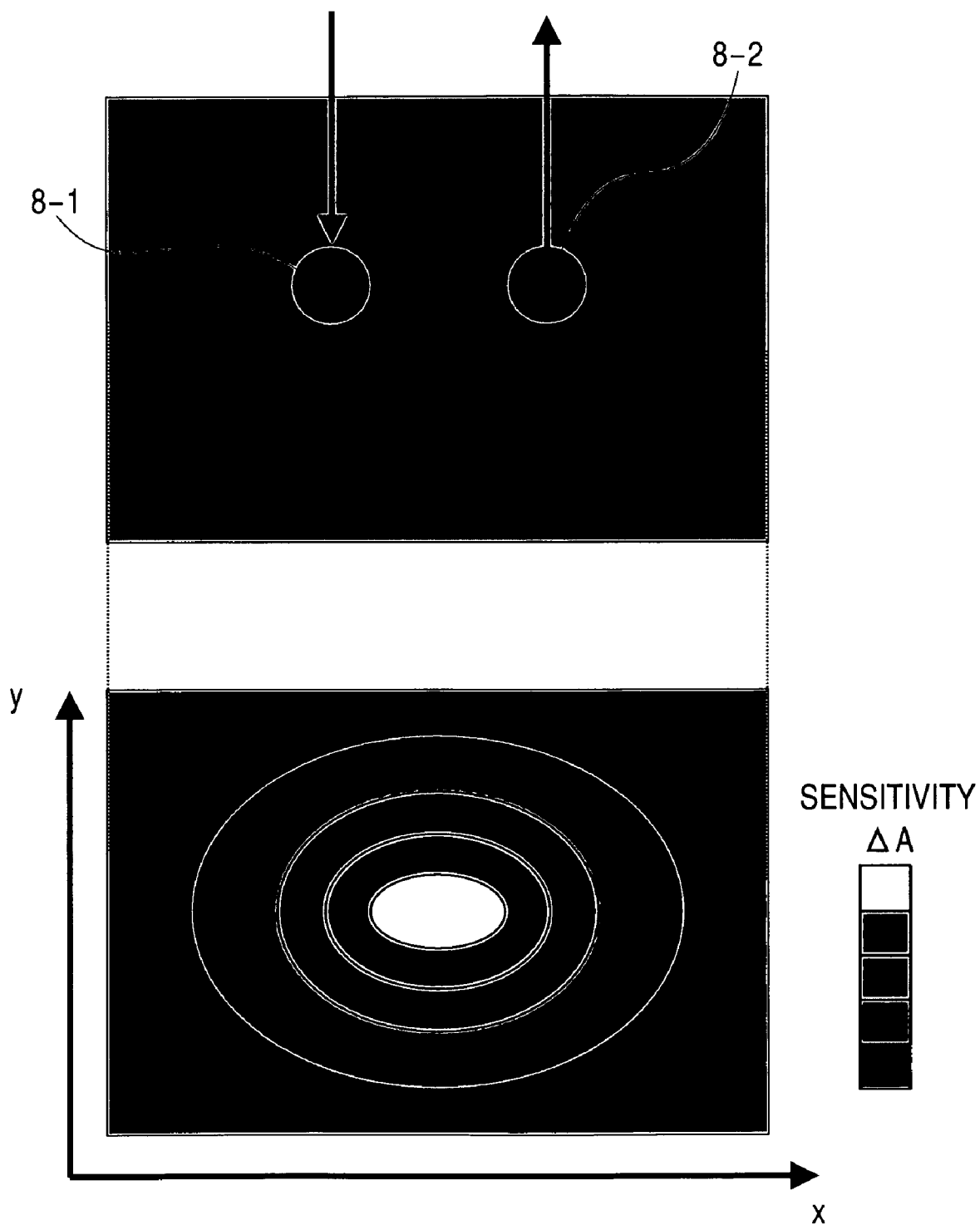
FIG. 8 is a diagram illustrating an exemplary sensitivity distribution characteristic.
Figure 9:
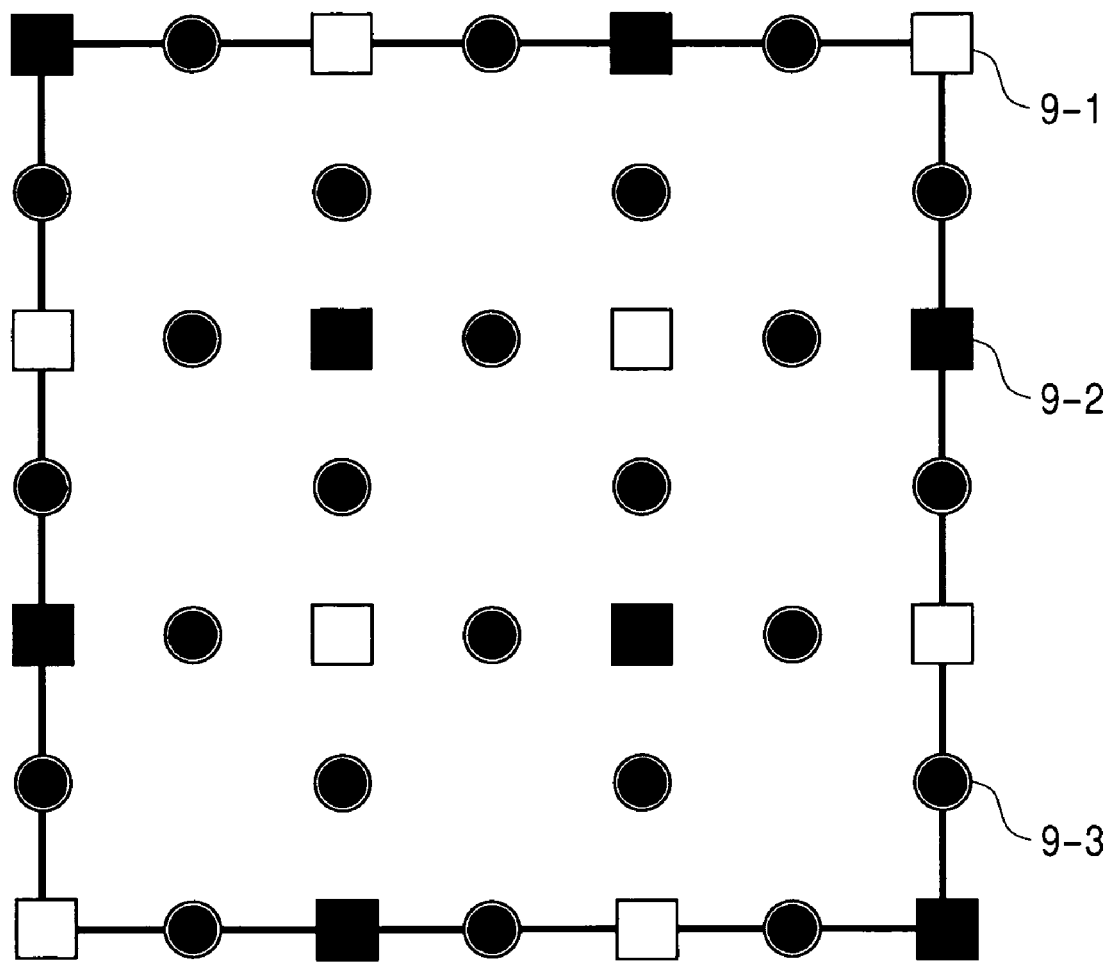
FIG. 9 is a diagram illustrating an exemplary spatial distribution of light sources, light detectors, and sampling points.

For this reason, another algorithm is proposed below. The distribution of displacements illustrated in FIG. 12 has been obtained by attaining displacements to the central point of the brain activation area. Therefore, there is a probability for discussion of the method for compensation for displacement in the case where the maximal area of the topographic image is established at the central point. In actuality, a user often determines the brain activation area from the maximal point thereof in the topographic image showing changes in blood volume. Accordingly, this method of the present invention discuses an algorithm for:

(1) extracting the maximal value of the topographic image from the image processes and determining the location of that point; and (2) compensating for the location of the extracted point using the distribution of displacements illustrated in FIG. 8.

Figure 15:
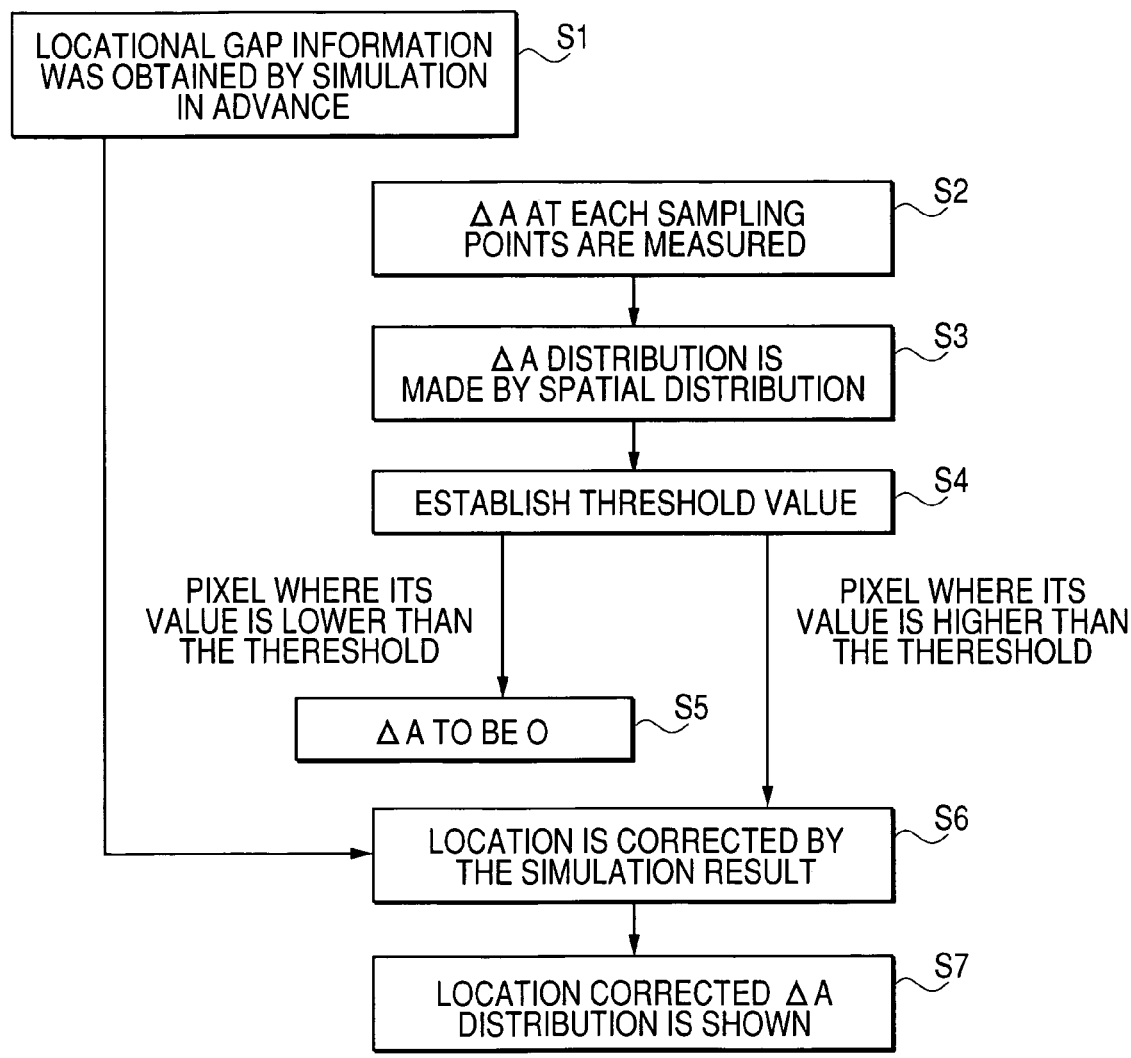
FIG. 15 is a diagram illustrating the flowchart indicating an algorithm for compensation of location accuracy.

More concretely, the following methodology is used as illustrated in the flowchart of FIG. 15.

1. Displacement information for each coordinate is collected by simulation before the system is utilized (S1 in FIG. 15).
2. Measurement of $\Delta A$ at each sampling point is made (S2 in FIG. 15).
3. A signal intensity distribution using the space interpolation process is generated (S3 in FIG. 15).
4. A threshold value is set (S4 in FIG. 15).
5. No signal intensity distribution for the coordinates having the intensity which is less than the threshold value are generated (S5 in FIG. 15).
6. A location compensation process based on the displacement information of each coordinate for the coordinates having the intensity which is larger than the threshold value is undertaken (S6 in FIG. 15).
7. Finally, a display of the signal intensity distribution after the compensation process is generated (S7 in FIG. 15).

Figure 1:
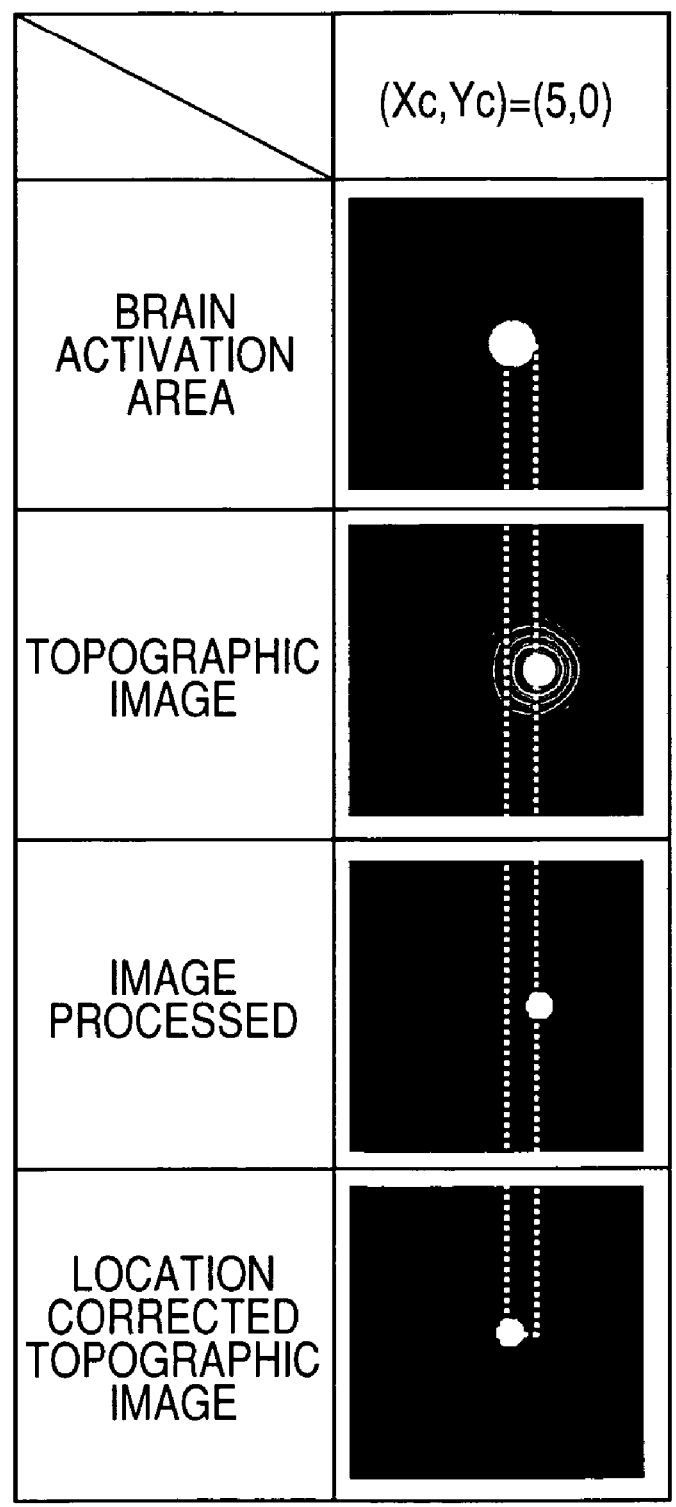
FIG. 1 is a diagram illustrating the results of compensation of the location accuracy.
Figure 16:
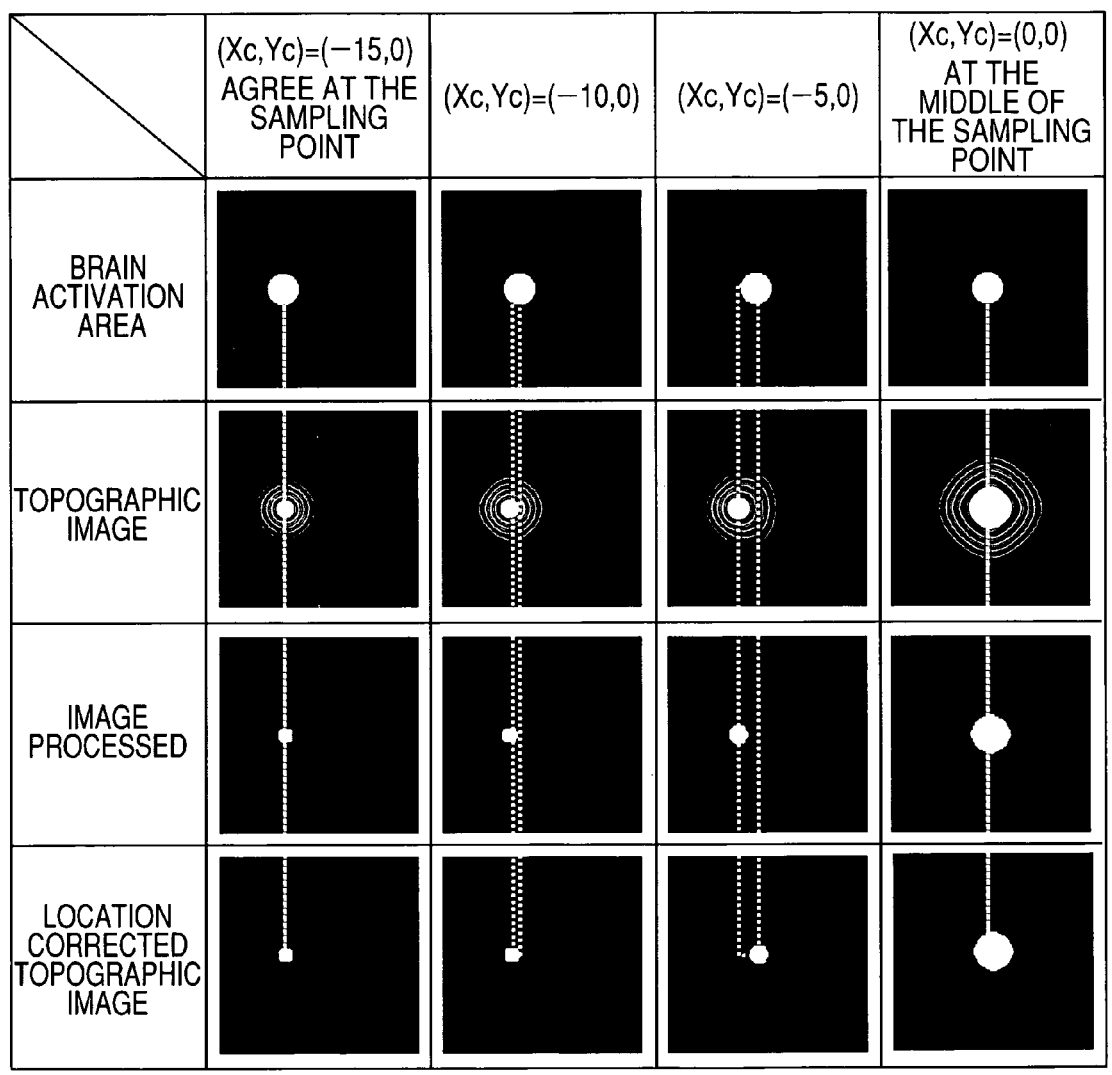
FIG. 16 is a diagram illustrating the result of compensating for location accuracy.
Figure 17:
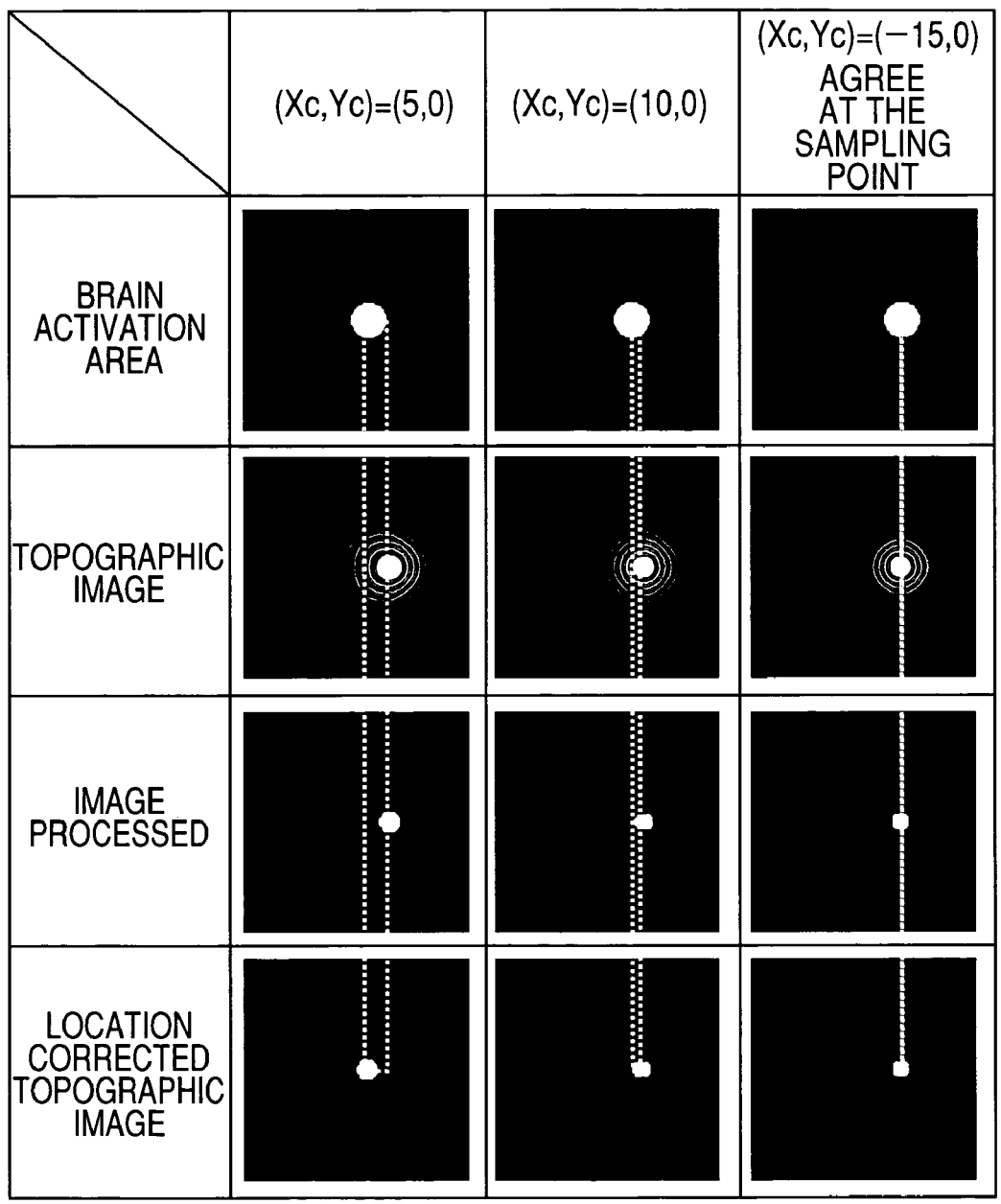
FIG. 17 is a diagram illustrating the result of compensating for location accuracy.

The results of testing the validity of this algorithm are illustrated in FIG. 1, FIG. 16, and FIG. 17. These figures illustrate (1) the brain activation area, (2) a topographic image indicating a change in blood volume in the brain activation area, (3) the results of a threshold process for the topographic image, and (4) the results of compensating for the location of the topographic image having completed the threshold process on the basis of the distributions of displacements of FIG. 11 and FIG. 12. Hereinafter, each figure will be described in detail.

(1) Binary Data Image Indicating the Brain Activation Area

Figure 10A:
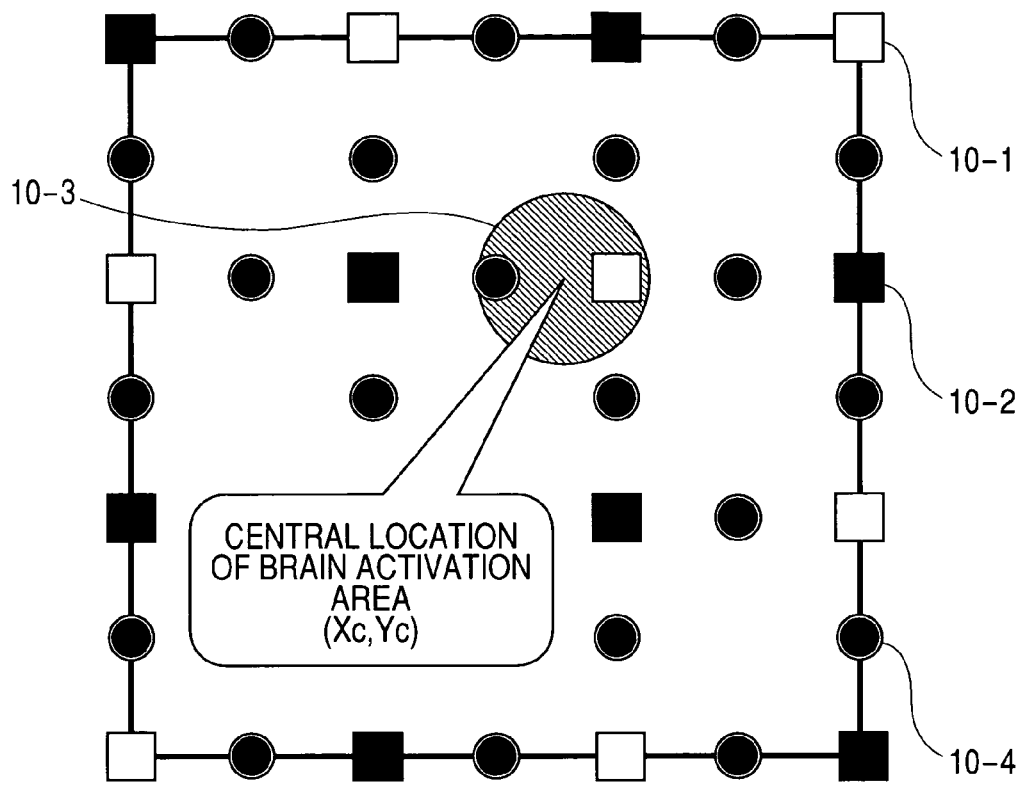
FIG. 10 illustrates the maximum points of a topographic image for the central area of brain activation obtained by computer simulation, including a spatial location diagram (FIG. 10A) and a topographic map (FIG. 10B)
Figure 10B:
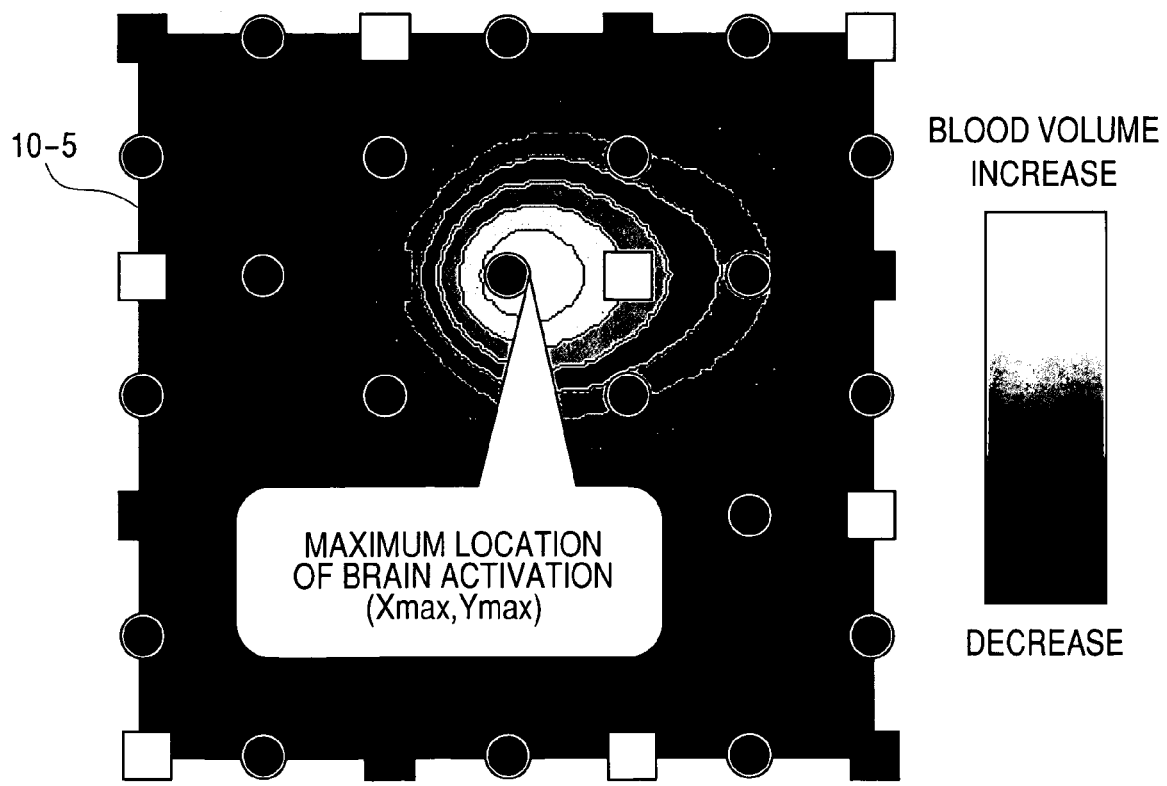

In the arrangement of the light source and the light detector illustrated in FIG. 10 (measurement area=90 mm×90 mm), a brain activation area with a diameter of 15 mm has been set at the inside of the measurement area. The size of this activation area with a diameter of 15 mm corresponds, for example, to the size of a human finger motor (the brain function existing on the cortex for controlling the motor function of the fingers).

(2) Topographic Image

The topographic image indicating the brain activation at the brain activation area described in step (1) has been generated with computer simulation. More concretely, changes in the degree of light absorption at the preset brain activation area are detected at the 24 sampling points illustrated in FIG. 4, and the spatial distributions of such changes are visualized as an image with the interpolation process.

(3) Result of Threshold Process of Topographic Image

With the threshold process, the topographic image described in step (2) is displayed as a binary data image. In this embodiment, the topographic image of step (2) is standardized by 1 to obtain the binary data image wherein the area having a value of at least 0.9 is defined as 1, and the area having any other values is defined as 0.

(4) Result of Location Compensation of the Image after the Threshold Process

The central point of the topographic image of step (3) has been compensated in accordance with the distribution of displacements illustrated in FIG. 11 and FIG. 12.

Referring to FIG. 1, a topographic image showing changes in the degree of light absorption at the brain activation area when (Xc, Yc) is (5, 0) has been generated. Since the sampling point nearest to (Xc, Yc)=(5, 0) exists at the point where (X, Y) is (15, 0), the topographic image is deformed in the manner that the image is attracted to this point. However, as a result of setting the threshold value to 0.9 and forming this topographic image as the binary data image, the circular image which is similar to the circular brain activation area shown at the original point has been obtained. That is, the image depicted in the column of the compensation for image location described above (Location corrected) has been obtained as a result of a parallel transfer of such circular image by obtaining the central point of image and changing the central point thereof in accordance with displacements of FIG. 8. The location of the image is almost matched with the original location. From this result, it can be noted that compensation for location has been realized.

Further, in view of discussing the validity of this algorithm, an improvement in the location accuracy based on this algorithm has been verified by setting the brain activation areas to seven areas including the brain activation areas of FIG. 1. The result of this verification is illustrated in FIG. 16 and FIG. 17. According to the results shown in these figures, since the original topographic image is not displaced under the condition that (Xc, Yc) is (±15, 0) and (0, 0), any improvement by the compensation using this algorithm cannot be detected. However, when (Xc, Yc)=(10, 0), (±5, 0), it is apparent that the location of the image in which the threshold value has been extracted and the location has been compensated is matched with the original brain activation area in comparison with the maximal point of the topographic image in which changes in blood volume at each sampling point has been space-interpolated. From this result, validity of the algorithm proposed has been confirmed.

Figure 18:
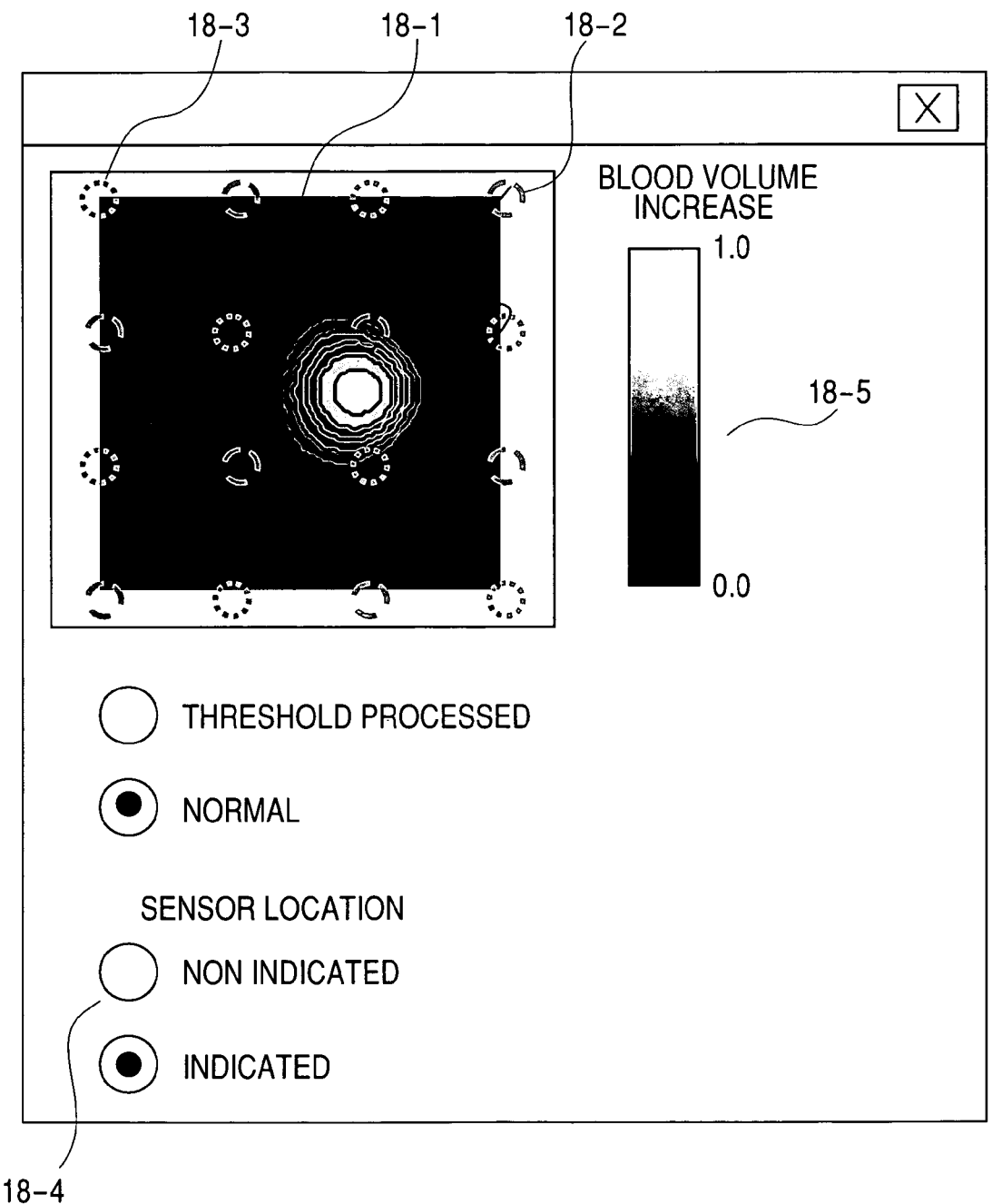
FIG. 18 is a diagram illustrating an exemplary display for a conventional topographic image.
Figure 19:
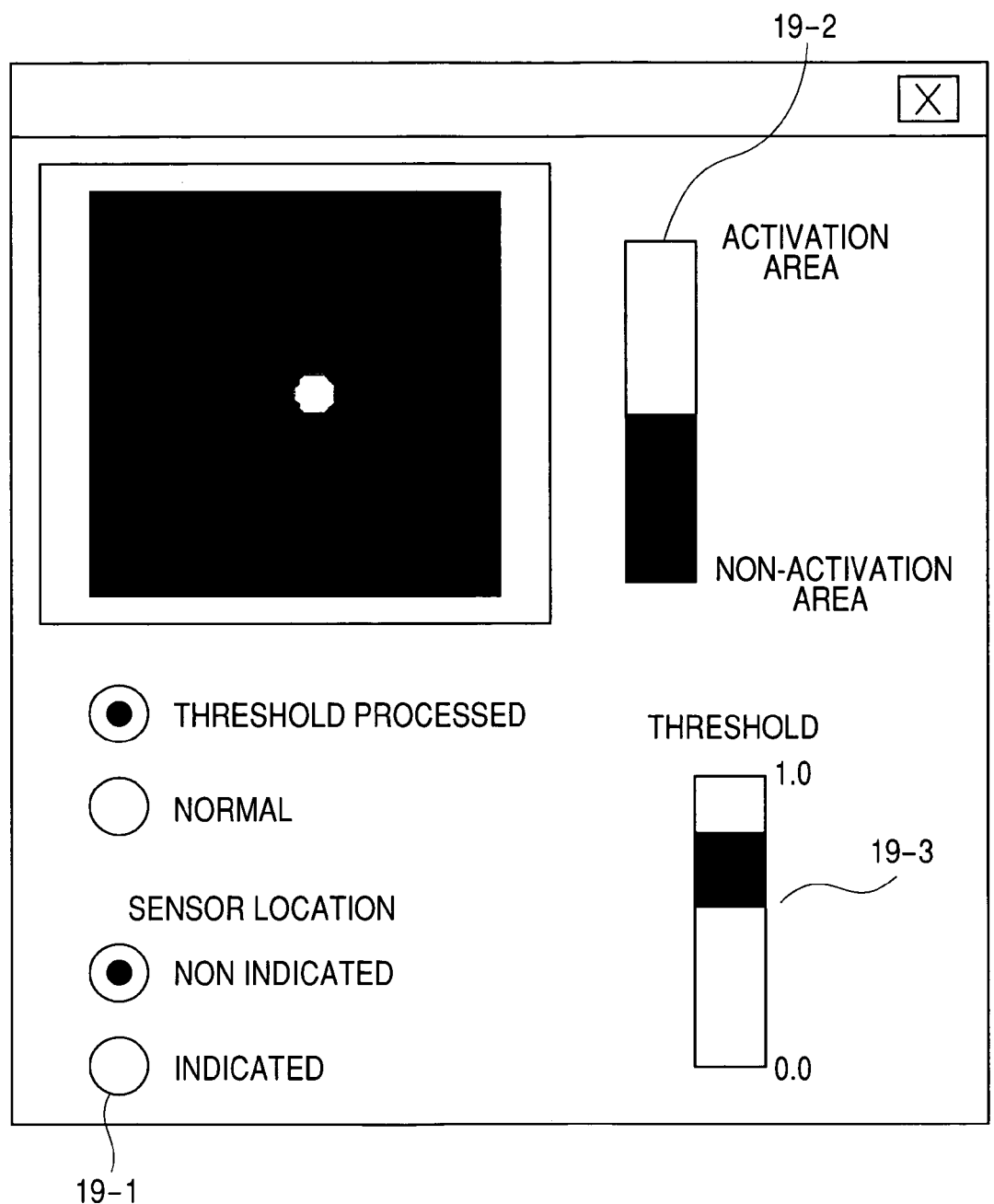
FIG. 19 is a diagram illustrating an example of the compensated image display method illustrated in FIG. 1, FIG. 16, and FIG. 17.
Figure 20:
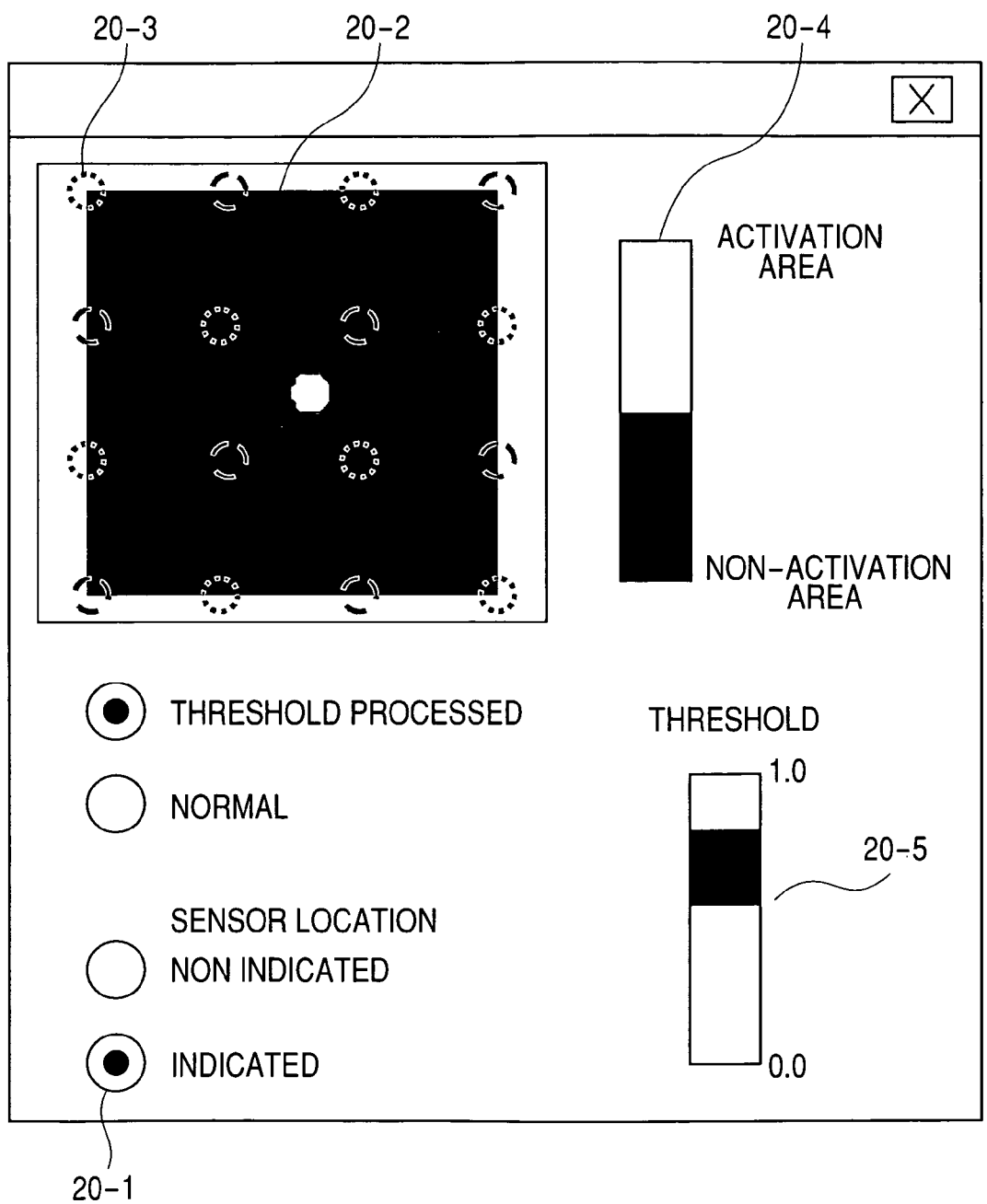
FIG. 20 is a diagram illustrating another example of the compensated image display method illustrated in FIG. 1, FIG. 16, and FIG. 17.
Figure 21:
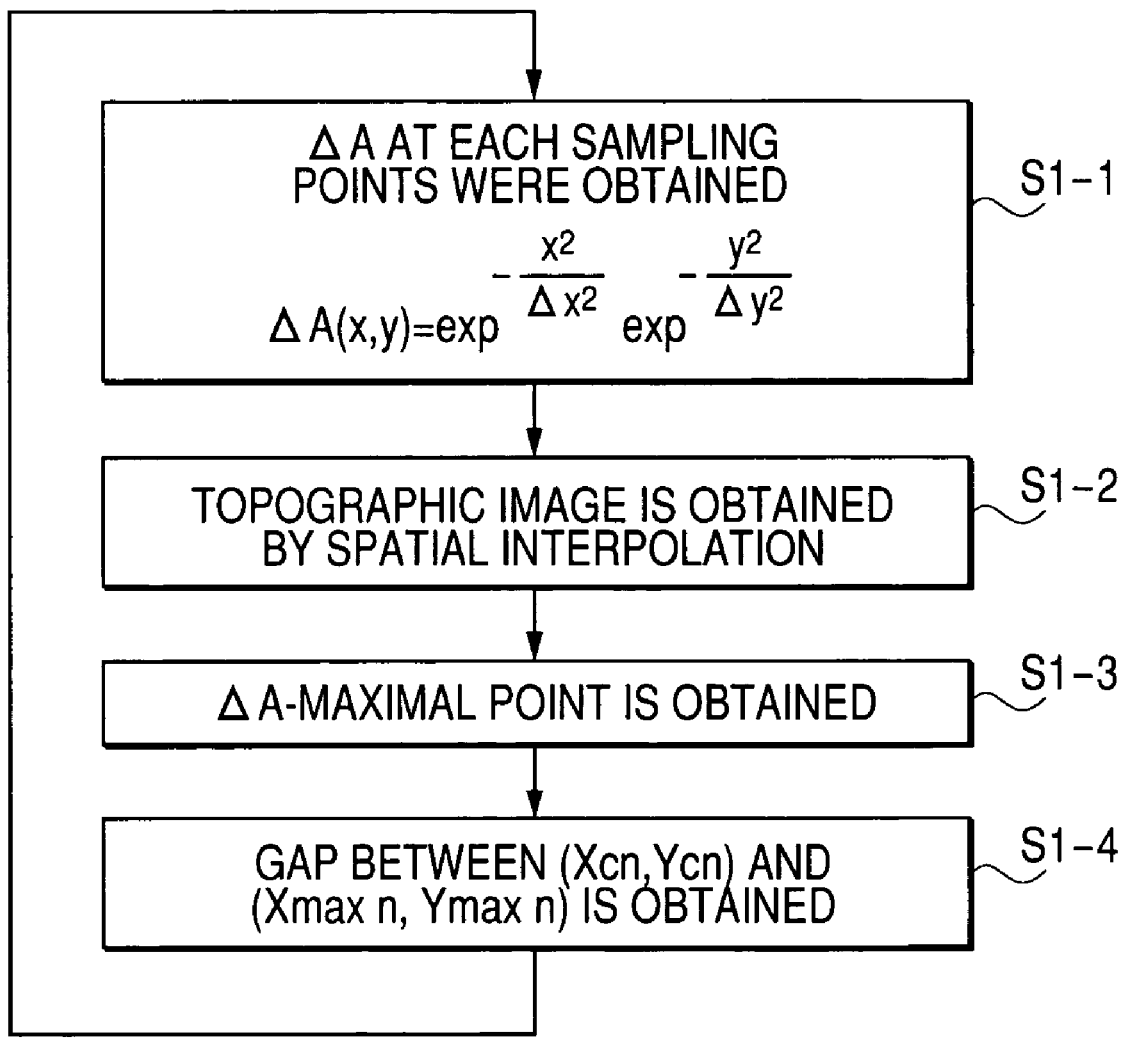
FIG. 21 is a flowchart for obtaining a distribution of the displacement information.

FIG. 18, FIG. 19, and FIG. 20 illustrate exemplary display images for implementing the algorithm described above. FIG. 18 is a display image format in which a conventional topographic image is displayed 18-1 designates a displayed topographic image in which the locations of the light source 18-2 and the light detector 18-3 are illustrated. Indicated and non-indicated conditions of locations of these light sources 18-2 and light detectors 18-3 can be selected and indication can be switched with a selection button 18-4. Moreover, a color bar 18-5 for showing the distribution of concentrations of this topographic image is also displayed on the display image to show a clear correspondence between the physical amounts and the colors of the topographic image. This color bar 18-5 has usually been subjected to the gradation process to easily observe the concentration of changes in blood volume.

FIG. 19 and FIG. 20 illustrate an embodiment of the present method of displaying the images compensated by the algorithm illustrated in FIG. 1, FIG. 16, and FIG. 17. This display image is referred to as the threshold processing mode. FIG. 19 does not show the locations of the light source and light detector, but FIG. 20 displays the locations of the light source 20-2 and the light detector 20-3 through the selecting operations of check boxes 19-1, 20-1. In these figures, 19-2 and 20-4 are color bars for showing the activation area and non-activation area. Unlike the color bar designated as 18-5, these color bars may be displayed with the binary data in place of the gradation display. The display of these color bars represents the display of the areas for activations of the brain.

In addition, 19-3 and 20-5 designate the bars for setting up the threshold for the image processes. In FIG. 18 and FIG. 19, the threshold is set to 0.9 to form the image with binary data in order to set 1 for the area of the threshold larger than this value and 0 for the area of the threshold not larger than this value. However, a problem is not generated even when the value 0.9 is freely set by a user. For example, when it is desired to observe only the central point of the brain activation area, it is sufficient to set the threshold to 1.0. However, on the contrary, when it is desired to remove a little of the "blur" of the topographic image, it is sufficient to set the threshold to a value near 0.0. As a result, a user is able to select the desired image display method.

Additionally, the present invention includes a computer program utilized in a living body light measurement system for measuring the inside of a subject by illuminating a plurality of areas of the subject with the light and detecting the light propagated within the subject at a plurality of areas of the subject. The computer program preferably causes a general purpose computer to carry out the following steps:

generate a distribution of signal intensity on the subject on the basis of the light signal detected at a plurality of areas;

execute the threshold process for generating a signal intensity distribution with an intensity equal to or greater than a predetermined threshold for the signal intensity distribution; and compensate for the displacement with the arithmetic process on the basis of the data, for the threshold processed signal intensity distribution, which is generated before the living body light measurement for displacement between the brain activation area and the maximal location of the signal intensity distribution generated when the signal intensity distribution is generated. Preferably, the threshold value is set by a user of the computer program.

Nothing in the above description is meant to limit the present invention to any specific materials, geometry, or orientation of elements. Many part/orientation substitutions are contemplated within the scope of the present invention and will be apparent to those skilled in the art. The embodiments described herein were presented by way of example only and should not be used to limit the scope of the invention.

Although the invention has been described in terms of particular embodiments in an application, one of ordinary skill in the art, in light of the teachings herein, can generate additional embodiments and modifications without departing from the spirit of, or exceeding the scope of, the claimed invention. Accordingly, it is understood that the drawings and the descriptions herein are proffered only to facilitate comprehension of the invention and should not be construed to limit the scope thereof.

What is claimed is:

1. A living body light measurement system, comprising:
   a plurality of light sources for illuminating a subject with light;
   a plurality of light detectors for detecting the light illuminated from said plurality of light sources after said light is propagated through the subject;
   a first arithmetic unit for generating a first signal intensity distribution for said subject based on the light signal detected with said plurality of light detectors;
   a second arithmetic unit for executing a threshold process to generate a second signal intensity distribution for signal intensities which are at least equal to a predetermined threshold for signal intensity distribution;
   a recording unit for storing data which defines a displacement between a brain activation area and a maximal location of the signal intensity distribution which is generated when said first arithmetic unit generates the first signal intensity distribution, wherein location information for said plurality of light sources and plurality of light detectors is obtained before said first signal intensity distribution is generated; and a third arithmetic unit for generating a third signal intensity distribution which utilizes the data stored in the recording unit to compensate for the displacement for the threshold-processed second signal intensity distribution.

2. The living body light measurement system according to claim 1, further comprising:
a display unit for displaying the third signal intensity distribution.

3. The living body light measurement system according to claim 1, further comprising:
a setting unit for setting said threshold.

4. The living body light measurement system according to claim 1, wherein said plurality of light sources and said plurality of light detectors are alternately located in the form of a lattice.

5. The living body light measurement system according to claim 1, further comprising:
a setting unit for selecting whether to display the third signal intensity distribution or the second signal intensity distribution.

6. A living body light measurement system comprising:
a plurality of light sources for illuminating a subject with light;
a plurality of light detectors for detecting the light illuminated from said plurality of light sources after said light is propagated through the subject;
a first arithmetic unit for generating a first signal intensity distribution for said subject based on the light signal detected with said plurality of light detectors;
a second arithmetic unit for executing a threshold process to generate a second signal intensity distribution for signal intensities which are at least equal to a predetermined threshold for signal intensity distribution;
a recording unit for storing data which defines a displacement between a brain activation area and a maximal location of the signal intensity distribution which is generated when said first arithmetic unit generates the first signal intensity distribution; and
a third arithmetic unit for generating a third signal intensity distribution which utilizes the data stored in the recording unit to compensate for the displacement for the threshold-processed second signal intensity distribution.

7. The living body light measurement system according to claim 6, further comprising:
a display unit for displaying the third signal intensity distribution.

8. The living body light measurement system according to claim 6, further comprising:
a setting unit for setting said threshold.

9. The living body light measurement system according to claim 6, wherein said plurality of light sources and said plurality of light detectors are alternately located in the form of a lattice.

10. The living body light measurement system according to claim 6, further comprising:
a setting unit for selecting whether to display the third signal intensity distribution or the second signal intensity distribution.

11. A signal processing method, utilized for a living body light measurement system for measuring an inside of a subject by illuminating light to a plurality of areas of the subject and detecting the light propagated through the inside of the subject, said method comprising the steps of:
generating data, from a computer simulation, of the displacement between a brain activation area and a maximal location of signal intensity distribution on the subject generated on the basis of the light signal detected at said plurality of areas;
illuminating the light to said plurality of areas of the subject;
detecting the light illuminated to the subject and propagated through the inside of the subject;
generating a first signal intensity distribution of the subject on the basis of the detected light;
executing a threshold process to generate a second signal intensity distribution of intensities which are at least equal to a predetermined threshold; and
compensating for a displacement based on the data generated from the computer simulation and creating a third threshold-processed signal intensity distribution.

12. The signal processing method according to claim 11, further comprising a step of:
displaying the third signal intensity distribution.

13. The signal processing method according to claim 11, wherein the threshold is a variable value which can be set by a user.

14. The signal processing method according to claim 11, wherein said plurality of locations for the illumination of the light and a plurality of locations for detection of the light are alternately located in the form of a lattice.

* * * * *